(12) United States Patent
Alimardanov et al.

(10) Patent No.: US 12,286,405 B2
(45) Date of Patent: Apr. 29, 2025

(54) SCALABLE SYNTHESIS OF DUAL-TARGET INHIBITOR OF CANNABINOID-1 RECEPTOR AND INDUCIBLE NITRIC OXIDE SYNTHASE

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Asaf Ragim Alimardanov, North Potomac, MD (US); Junfeng Huang, Woodstock, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 816 days.

(21) Appl. No.: 17/610,537

(22) PCT Filed: Apr. 30, 2020

(86) PCT No.: PCT/US2020/030624
§ 371 (c)(1),
(2) Date: Nov. 11, 2021

(87) PCT Pub. No.: WO2020/236411
PCT Pub. Date: Nov. 26, 2020

(65) Prior Publication Data
US 2022/0227714 A1    Jul. 21, 2022

Related U.S. Application Data

(60) Provisional application No. 62/849,193, filed on May 17, 2019.

(51) Int. Cl.
*C07D 231/06* (2006.01)

(52) U.S. Cl.
CPC ........ *C07D 231/06* (2013.01); *C07B 2200/07* (2013.01)

(58) Field of Classification Search
CPC .... C07D 231/06; C07B 2200/07; A61P 25/00
USPC ...................................................... 548/379.4
See application file for complete search history.

(56) References Cited

FOREIGN PATENT DOCUMENTS

WO    2010012797 A2    2/2010
WO    2016196646 A1    12/2016

OTHER PUBLICATIONS

Aldrich, Aldrich Catalogue, 1998-1999, pp. 756, 1326, and 1430, pp. 4 (Year: 1999).*
International Search Report issued in Application No. PCT/US2020/030624 on Jul. 17, 2020, 6 pages.
Malliga R. Iyer et al., "Design, Synthesis, and Biological Evaluation of Novel, Non-Brain-Penetrant, Hybrid Cannabinoid CB1R Inverse Agonist/Inducible Nitric Oxide Synthase (iNOS) Inhibitors for the Treatment of Liver Fibrosis", Journal of Medicinal Chemistry, vol. 60, 2017, pp. 1126-1141.
Malliga R. Iyer et al., Synthesis of 13C6-labeled, dual target inhibitor of cannabinoid-1 receptor (CB1R) and inducible nitric oxide synthase (iNOS), Journal of Labelled Compounds and Radiopharmaceuticals, vol. 61, 2018, pp. 773-779.
Written Opinion issued in Application No. PCT/US2020/030624 on Jul. 17, 2020, 11 pages.

* cited by examiner

*Primary Examiner* — Taylor V Oh
(74) *Attorney, Agent, or Firm* — CANTOR COLBURN LLP

(57) ABSTRACT

A process for the preparation of racemic and optically active (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide in high enantiomerical purity is provided.

24 Claims, No Drawings

SCALABLE SYNTHESIS OF DUAL-TARGET INHIBITOR OF CANNABINOID-1 RECEPTOR AND INDUCIBLE NITRIC OXIDE SYNTHASE

CROSS-REFERENCE TO RELATED APPLICATIONS

This application is U.S. National Phase of International Patent Application No. PCT/US2020/030624 filed Apr. 30, 2020, which claims priority under 35 U.S.C. § 119 (e) to U.S. Provisional Application Ser. No. 62/849,193, filed May 17, 2019, the disclosures of which are incorporated herein by reference in their entirety.

BACKGROUND OF THE INVENTION

Field of Invention

The present invention is directed to a synthesis of a dual-target inhibitor of cannabinoid-1 receptor and inducible nitric oxide synthase, and more specifically, to an improved process for synthesis of (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

Brief Description of Related Art

Cannabinoid-1 receptor ($CB_1R$) antagonists/inverse agonists have great potential in the treatment of obesity, diabetes, and other metabolic syndromes. $CB_1R$ agonists are also effective in mitigating fibrotic disorders. Despite the promising therapeutic effects, $CB_1R$ antagonists/inverse agonists found limited clinical use due to their ability to induce CNS-mediated adverse events such as anxiety and development of suicidal tendencies.

Inducible nitric oxide synthase (iNOS) is another promising target implicated in fibrotic and inflammatory disorders. A hybrid compound inhibiting both $CB_1R$ and iNOS was postulated to have beneficial effects in mitigating fibrosis and its related complications without any adverse effects. Peripheral restriction of hybrid $CB_1R$/iNOS inhibitors proved to be of critical importance to minimize any neuropsychiatric side effects secondary to blockade of $CB_1R$ in the CNS. Peripheral restriction of these compounds also precludes their ability to reduce brain iNOS activity, which has been proposed to aggravate certain neuroinflammatory conditions.

As a result of the discovery efforts, (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide (S)-1 (MRI-1867) has been reported as a potent and selective, peripherally acting dual-target $CB_1R$/iNOS inhibitor. The compound demonstrated potent in vivo pharmacological activities such as reduction of food intake mediated by the $CB_1R$ antagonism and antifibrotic effect in the animal models of fibrosis mediated by iNOS inhibition and $CB_1R$ antagonism. It was also found that (S)-MRI-1867 has potential for treatment of Hermansky-Pudlak syndrome (HPS), a rare genetic disorder characterized by blood platelet disfunction with prolonged bleeding, visual impairment, and abnormally light coloring of the skin, hair, and eyes (a condition known as oculocutaneous albinism).

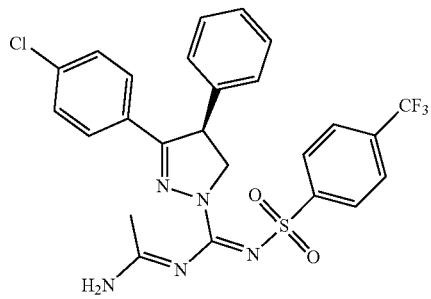
(S)-1

A racemic approach to MRI-1867 has been developed by Iyer et al. (*J. Med. Chem.* 2017, 60, 1126-1141 and *J. Label. Compd. Radiopharm.* 2018, 61, 773-779). However, the synthesis was low-yielding and included hazardous materials and cryogenic conditions, which made its large scale implementation difficult. In addition, the desired (S)-MRI-1867 had to be separated from its enantiomer via expensive and low-throughput preparative chiral HPLC or SFC.

There remains a need for an efficient, high-yielding, and scalable synthetic approach to provide substantial amounts of enantiomerically pure (S)-MRI-1867 for biological evaluation and clinical studies.

SUMMARY OF THE INVENTION

In an embodiment, a process for the preparation of (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide is provided. The process includes the steps of:
providing a compound

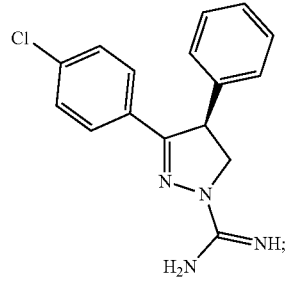 [SMILES: N=C(N)N1C[C@H](c2ccccc2)C(c2ccc(Cl)cc2)=N1]

and
converting the compound

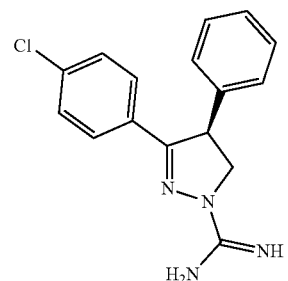

to (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

In another embodiment, a process for the preparation of (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide is provided. The process includes the steps of:

providing a compound

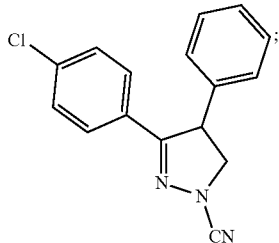 [SMILES: N#CN1CC(c2ccccc2)C(c2ccc(Cl)cc2)=N1]

and
converting the compound

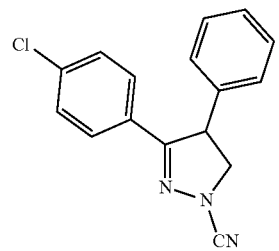 [SMILES: N#CN1CC(c2ccccc2)C(c2ccc(Cl)cc2)=N1]

to (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

In still another embodiment, a process for the preparation of (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide includes the steps of:

reacting 4-(trifluoromethyl)benzenesulfonamide with ethyl chloroformate to form ethyl (4-(trifluoromethyl)phenyl)sulfonylcarbamate;

reacting ethyl (4-(trifluoromethyl)phenyl)sulfonylcarbamate with compound

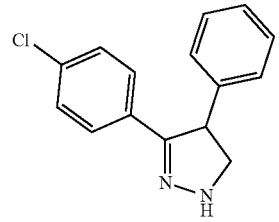 [SMILES: Clc1ccc(C2=NNCC2c2ccccc2)cc1]

to form compound

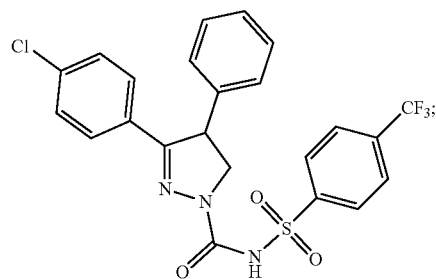 [SMILES: O=C(NS(=O)(=O)c1ccc(C(F)(F)F)cc1)N1CC(c2ccccc2)C(c2ccc(Cl)cc2)=N1]

reacting the compound

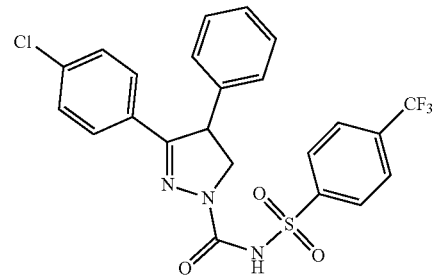 [SMILES: O=C(NS(=O)(=O)c1ccc(C(F)(F)F)cc1)N1CC(c2ccccc2)C(c2ccc(Cl)cc2)=N1]

with phosphorus oxychloride to form compound

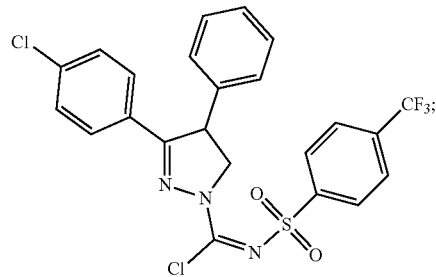 [SMILES: O=S(=O)(/N=C(/Cl)N1CC(c2ccccc2)C(c2ccc(Cl)cc2)=N1)c1ccc(C(F)(F)F)cc1]

and
converting the compound

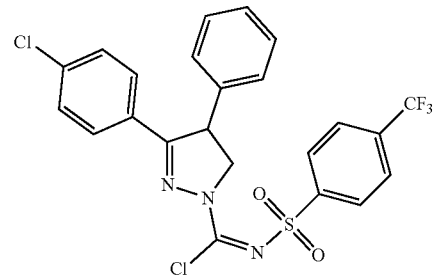 [SMILES: O=S(=O)(/N=C(/Cl)N1CC(c2ccccc2)C(c2ccc(Cl)cc2)=N1)c1ccc(C(F)(F)F)cc1]

to (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

In yet another embodiment, provided is a compound represented by one of the following formulae:

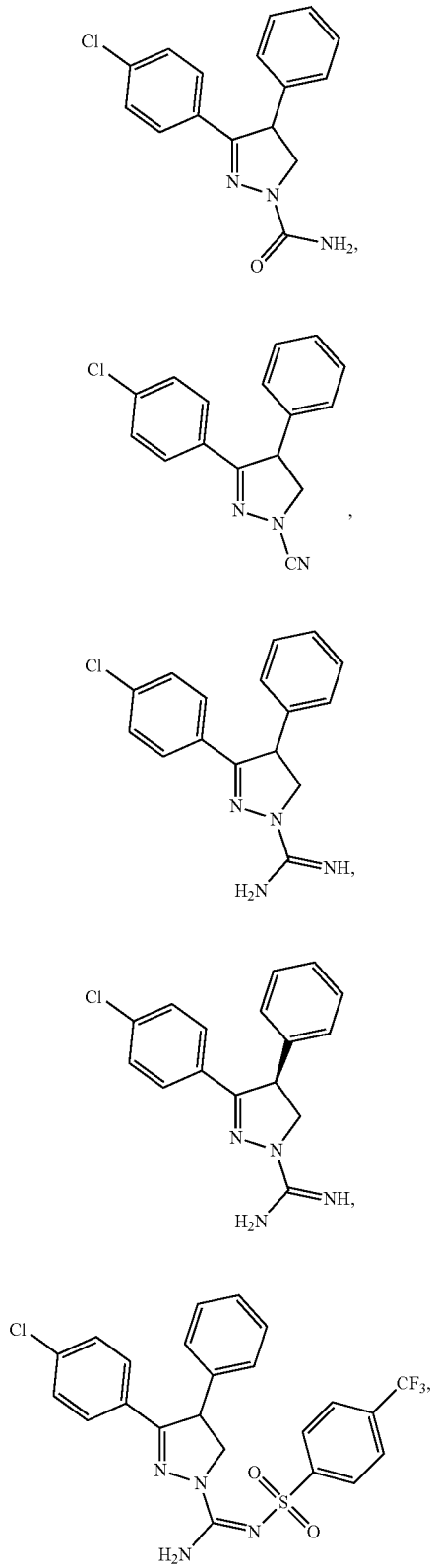

-continued

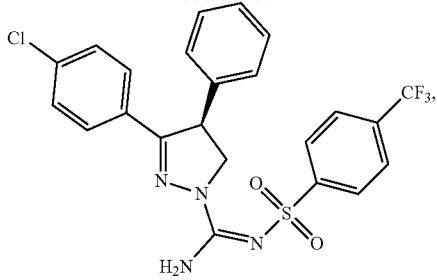

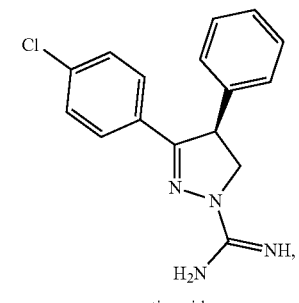

aspartic acid salt

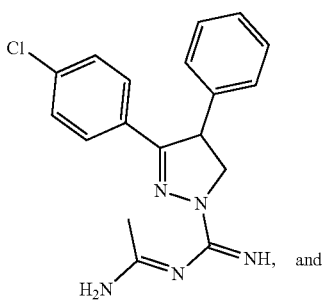
and

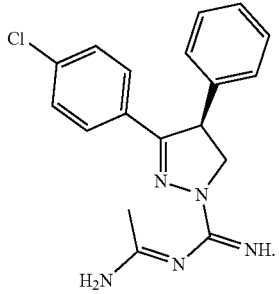

DETAILED DESCRIPTION

Reference will now be made in detail to embodiments, which may have different forms and should not be construed as being limited to the descriptions set forth herein. Accordingly, the embodiments are merely described below to explain aspects of the present description. As used herein, the term "and/or" includes any and all combinations of one or more of the associated listed items.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/ or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the term "alkyl group" refers to a group derived from a straight or branched chain saturated aliphatic hydrocarbon having the specified number of carbon atoms and having a valence of at least one.

As used herein, the term "cycloalkyl group" refers to a monovalent group having one or more saturated rings in which all ring members are carbon.

As used herein, the term "aryl," which is used alone or in combination, refers to an aromatic hydrocarbon containing at least one ring and having the specified number of carbon atoms. The term "aryl" may be construed as including a group with an aromatic ring fused to at least one cycloalkyl ring.

As used herein, the term "aryl," which is used alone or in combination, refers to an aryl group including carbon and 1 to 3 heteroatoms selected from the group consisting of N, O, S, and P as ring atoms.

As used herein, the term "substituted" means including at least one substituent such as a halogen (F, Cl, Br, I), hydroxyl, amino, thiol, carboxyl, carboxylate, ester (including acrylates, methacrylates, and lactones), ketone, anhydride, amide, nitrile, sulfide, disulfide, sulfone, sulfoxide, sulfonamide, nitro, $C_{1-20}$ alkyl, $C_{1-20}$ cycloalkyl (including adamantyl), $C_{1-20}$ alkenyl (including norbornenyl), $C_{1-20}$ alkoxy, $C_{2-20}$ alkenoxy (including vinyl ether), $C_{6-30}$ aryl, $C_{6-30}$ aryloxy, $C_{7-30}$ alkylaryl, or $C_{7-30}$ alkylaryloxy.

The existing sequence for the synthesis of racemic (1E, NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide (*J. Med. Chem.* 2017, 60, 1126-1141 and *J. Label. Compd. Radiopharm.* 2018, 61, 773-779) is shown in Scheme 1. The synthesis began with the reaction between 4-(trifluoromethyl)benzenesulfonamide 2 with methyl chloroformate to provide sulfonyl methyl carbamate 3a, which is then coupled with 4,5-dihydro-1H-pyrazole derivative 4 to yield sulfonyl urea product 5. The product 5 was subjected to phosphorus pentachloride ($PCl_5$) treatment in refluxing chlorobenzene to yield a sensitive imidoyl chloride 6 which was immediately treated in situ without purification with acetimidamide to yield racemic MRI-1867 (rac-1). The desired (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide was then obtained by a chiral high-pressure liquid chromatography (HPLC) or supercritical fluid chromatography (SFC) separation of the racemic mixture.

The reported synthesis has a number of shortcomings that made its large scale application problematic. For example, conversion of the sulfonyl urea product 5 to the imidoyl chloride 6 utilized a hazardous high-temperature mixture of phosphorus pentachloride and chlorobenzene. The reaction of the imidoyl chloride 6 with acetimidamide required cryogenic conditions (−78° C.). Further, the final yield of the racemic MRI-1867 based on the starting 4-(trifluoromethyl)benzenesulfonamide was only 18%.

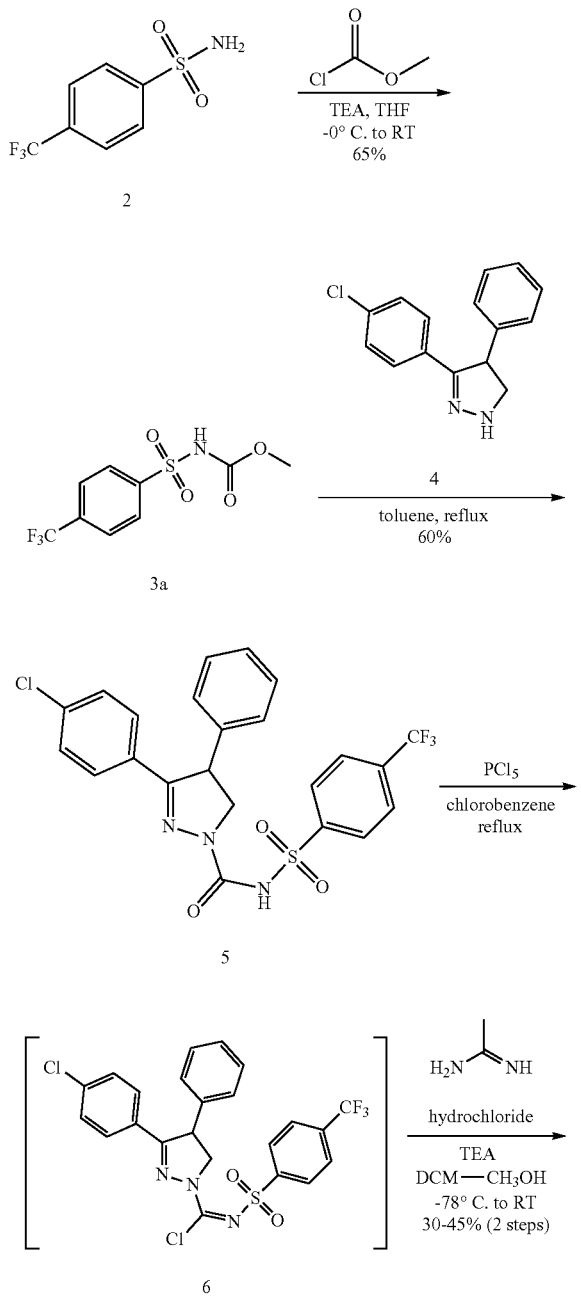

Scheme 1

-continued

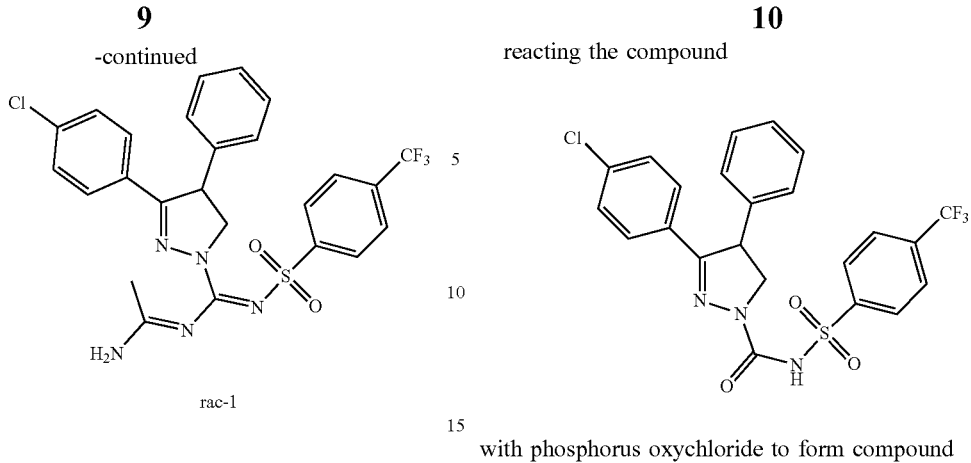

rac-1

The present inventors have discovered scalable synthetic approaches that resulted in substantial improvement of the published procedure.

In one of these approaches, according to an embodiment, a process for the preparation of (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide, may include the steps of:

reacting 4-(trifluoromethyl)benzenesulfonamide with ethyl chloroformate to form ethyl (4-(trifluoromethyl)phenyl)sulfonylcarbamate;

reacting ethyl (4-(trifluoromethyl)phenyl)sulfonylcarbamate with compound

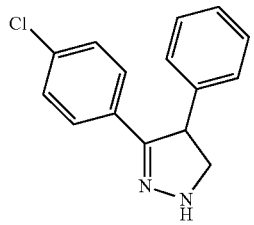 [SMILES: Clc1ccc(C2=NNCC2c2ccccc2)cc1]

to form compound

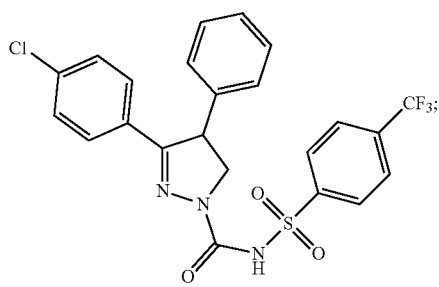 [SMILES: O=C(NS(=O)(=O)c1ccc(C(F)(F)F)cc1)N1CC(c2ccccc2)C(c2ccc(Cl)cc2)=N1]

reacting the compound

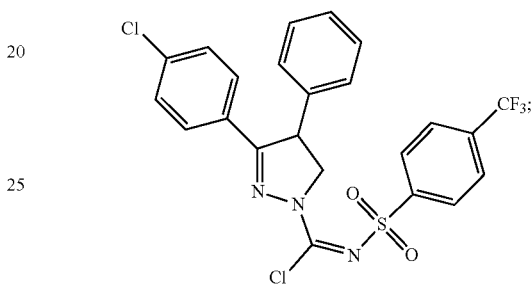

with phosphorus oxychloride to form compound

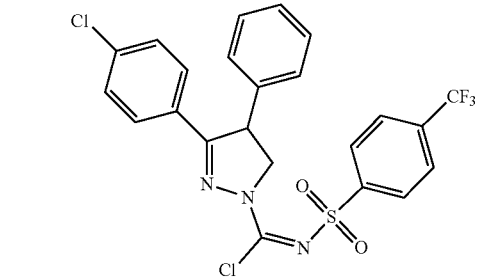 [SMILES: O=S(=O)(/N=C(/Cl)N1CC(c2ccccc2)C(c2ccc(Cl)cc2)=N1)c1ccc(C(F)(F)F)cc1]

and
converting the compound

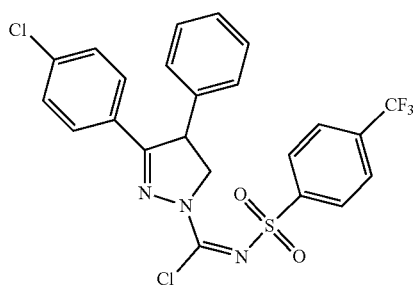 [SMILES: O=S(=O)(/N=C(/Cl)N1CC(c2ccccc2)C(c2ccc(Cl)cc2)=N1)c1ccc(C(F)(F)F)cc1]

to (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

The step of converting the compound to (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide may include:

reacting the compound

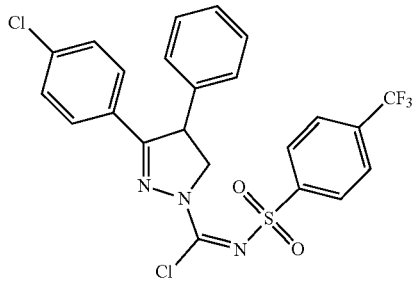 [SMILES: O=S(=O)(/N=C(/Cl)N1CC(c2ccccc2)C(c2ccc(Cl)cc2)=N1)c1ccc(C(F)(F)F)cc1]

with an acetimidamide agent in a solvent system comprising iso-propanol and dichloromethane to form (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

According to this approach (shown in Scheme 2), use of a more stable ethyl chloroformate instead of methyl chloroformate results in a significant increase in yield of the sulfonyl carbamate 3b and the sulfonyl urea product 5 in the following step. A combination of phosphorus oxychloride and N,N-diisopropylethylamine, in place of phosphorus pentachloride and chlorobenzene, affords a much easier control of the reaction conditions to obtain the intermediate imidoyl chloride 6. Finally, implementation of the iso-propanol-dichloromethane solvent system provides a smooth conversion of the intermediate imidoyl chloride 5 to racemic MRI-1867 in a at least 70% yield and at least 99% purity over the two steps.

Scheme 2

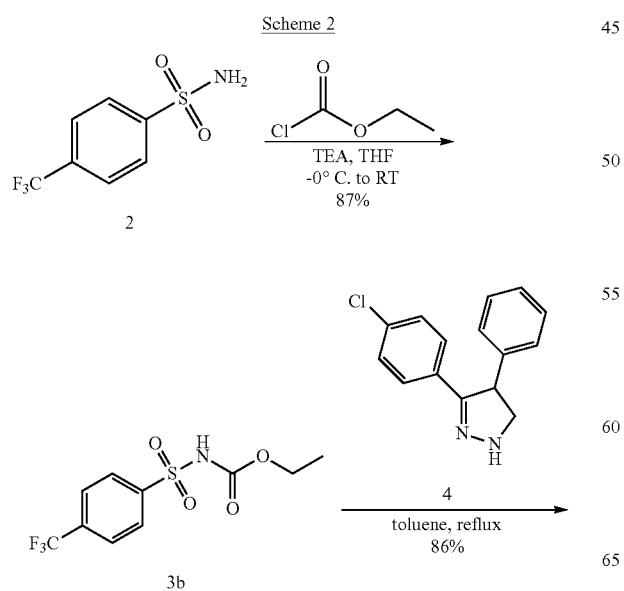

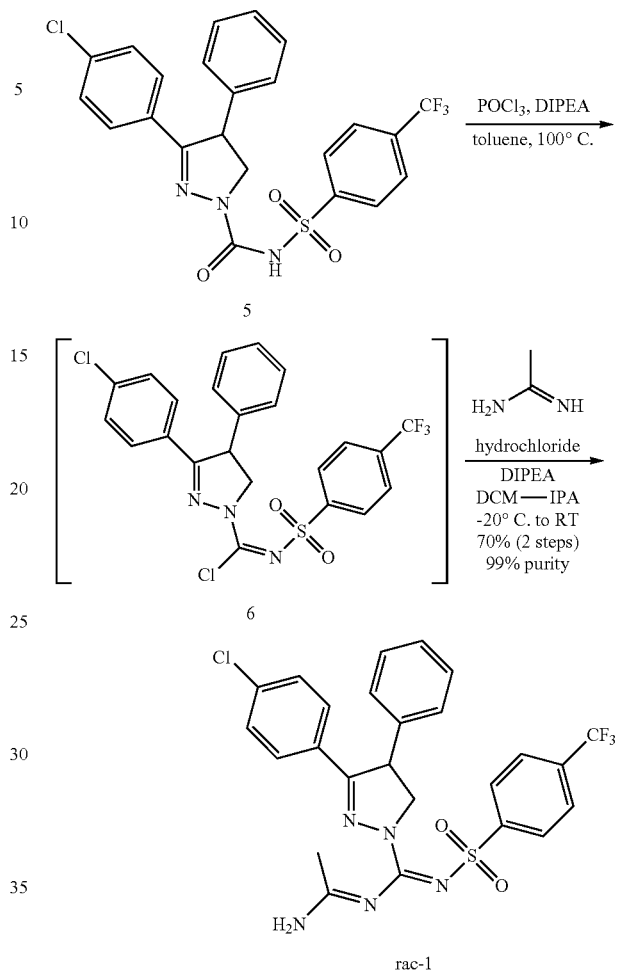

Herein, a process for the preparation of racemic (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide (rac-1) is thereby provided. The process includes:

Step (a): reacting 4-(trifluoromethyl)benzenesulfonamide with ethyl chloroformate to form ethyl (4-(trifluoromethyl)phenyl)sulfonylcarbamate;

Step (b): reacting ethyl (4-(trifluoromethyl)phenyl)sulfonylcarbamate with compound

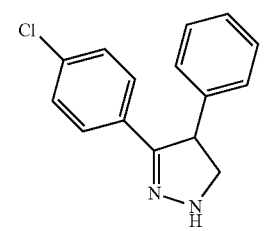 [SMILES: Clc1ccc(C2=NNCC2c2ccccc2)cc1]

to form compound

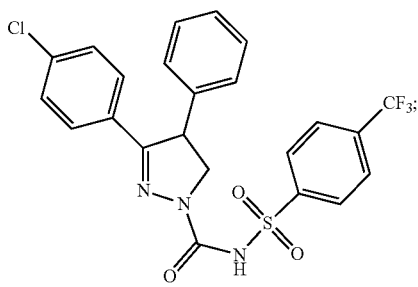 [SMILES: O=C(NS(=O)(=O)c1ccc(C(F)(F)F)cc1)N1CC(c2ccccc2)C(c2ccc(Cl)cc2)=N1]

Step (c): reacting the compound

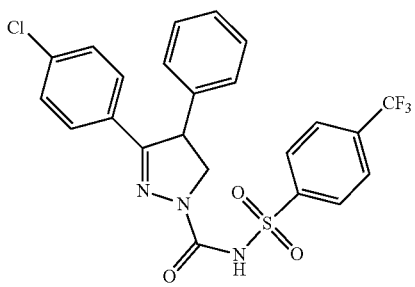 [SMILES: O=C(NS(=O)(=O)c1ccc(C(F)(F)F)cc1)N1CC(c2ccccc2)C(c2ccc(Cl)cc2)=N1]

with phosphorus oxychloride to form compound

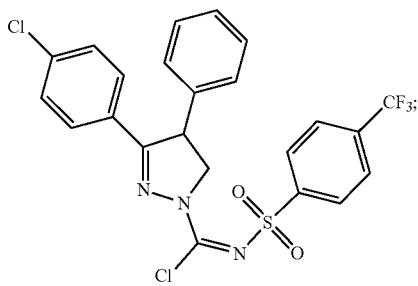 [SMILES: O=S(=O)(/N=C(/Cl)N1CC(c2ccccc2)C(c2ccc(Cl)cc2)=N1)c1ccc(C(F)(F)F)cc1]

and

Step (d): reacting the compound

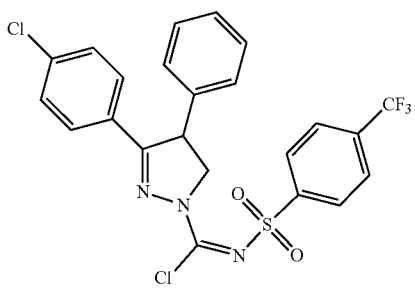 [SMILES: O=S(=O)(/N=C(/Cl)N1CC(c2ccccc2)C(c2ccc(Cl)cc2)=N1)c1ccc(C(F)(F)F)cc1]

with an acetimidamide agent in a solvent system including iso-propanol and dichloromethane to form (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

In Step (a), use of a more stable ethyl chloroformate in place of methyl chloroformate (as in the published synthesis) results in a substantial increase in yield of the sulfonyl carbamate 3b (87% versus 65% in the published synthesis). The reaction can be carried out in tetrahydrofuran (THF) in the presence of a tertiary amine such as triethylamine (TEA), wherein the addition of the reagents takes place at 0° C. followed a warm up to room temperature and stirring overnight.

In Step (b), use of ethyl sulfonyl carbamate 3b results in substantial increase in the yield of the sulfonyl urea product 4 (86% versus 60% in the published synthesis). The reaction can be carried out in toluene under reflux for about 4 hours.

In Step (c), a combination of phosphorus oxychloride (POCl$_3$) and N,N-diisopropylethylamine (DIPEA) (in place of phosphorus pentachloride and chlorobenzene in the original synthesis), affords a much easier control of the reaction conditions to provide the intermediate imidoyl chloride 5, which can be used in the next step without purification.

In Step (d), upon treatment with acetimidamide, the intermediate imidoyl chloride 5 undergoes a smooth conversion to rac-1. The implementation of the iso-propanol-dichloromethane ((IPA-DCM) solvent system results in reduced by-product formation, increasing the yield of rac-1 to about 70% versus 30-45% in the published synthesis. By using the synthesis rac-1 can be obtained in at least 99% purity.

The optically active (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide and the corresponding (R)-enantiomer can then be obtained by a chiral high-pressure liquid chromatography (HPLC) or supercritical fluid chromatography (SFC) separation of rac-1.

In another approach, according to an embodiment, a process for the preparation of (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide may include the steps of:

providing a compound

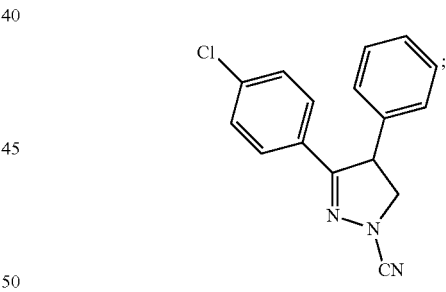

and converting the compound

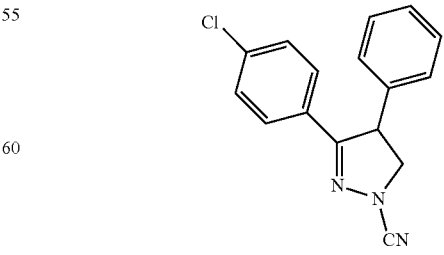

to (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

The step of providing a compound

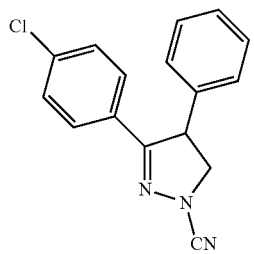

may include:
converting a compound

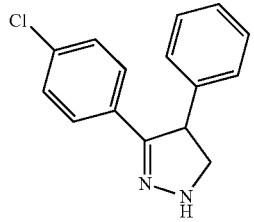

to a compound

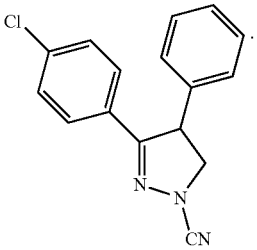 [SMILES: N#CN1CC(c2ccccc2)C(c2ccc(Cl)cc2)=N1]

The step of converting the compound

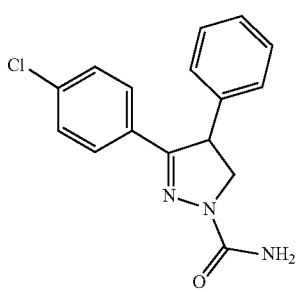 [SMILES: NC(=O)N1CC(c2ccccc2)C(c2ccc(Cl)cc2)=N1]

to the compound

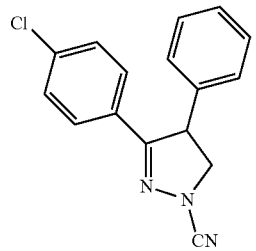 [SMILES: N#CN1CC(c2ccccc2)C(c2ccc(Cl)cc2)=N1]

may be carried out by contacting the compound

with a dehydrating agent.
The step of converting the compound

to (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide may include:
reacting the compound

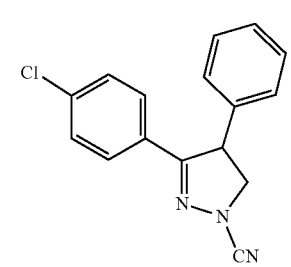 [SMILES: N#CN1CC(c2ccccc2)C(c2ccc(Cl)cc2)=N1]

with an acetimidamide agent to form a compound

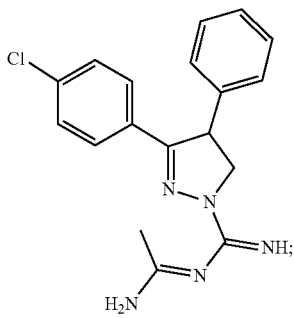 [SMILES: C/C(N)=N\C(=N)N1CC(c2ccccc2)C(c2ccc(Cl)cc2)=N1]

and
reacting the compound

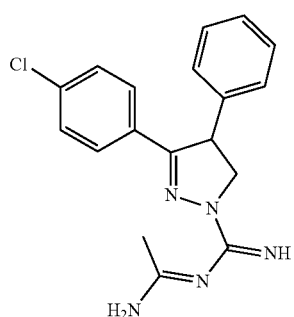

with a compound

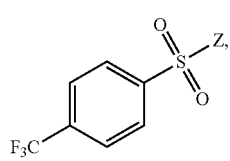

wherein Z is a third leaving group, to form (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

In this another approach (shown in Scheme 3), a reaction of the 4,5-dihydro-1H-pyrazole derivative 4 with an isocyanate agent gives the cyclic urea derivative 7, which undergoes dehydration to provide cyano derivative 11. The cyano derivative 11 may then be treated with an acetamidine salt in the presence of an amine to yield sensitive intermediate 12, which reacts with 4-(trifluoromethyl)benzenesulfonyl chloride 13 to give racemic MRI-1867 (rac-1).

Scheme 3

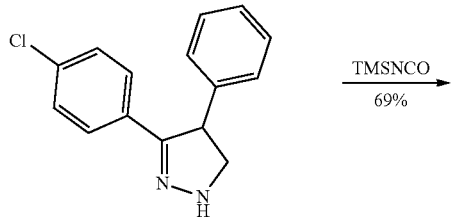

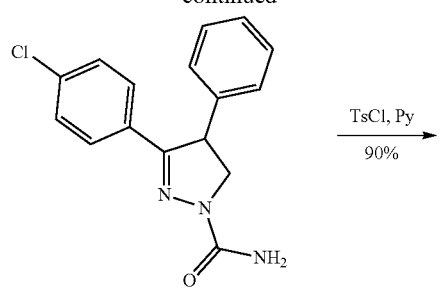

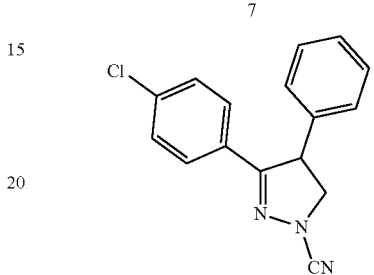

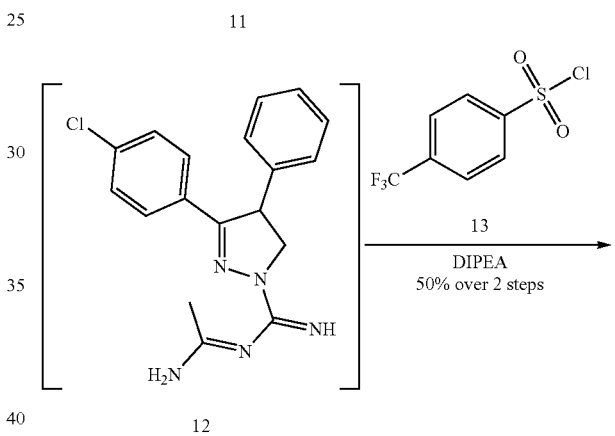

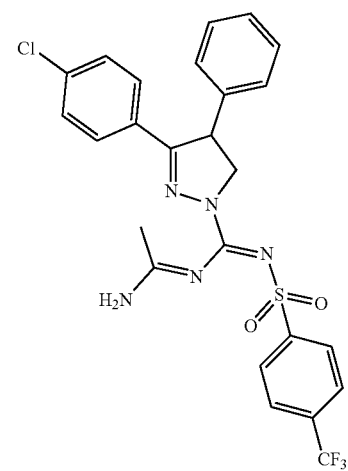

rac-(1)

Herein, a process for the preparation of (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide (rac-1) is thereby provided. The process includes:

Step (a): converting a compound

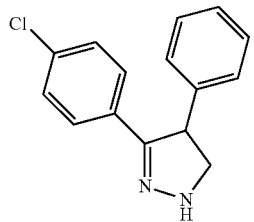 [SMILES: Clc1ccc(C2=NNCC2c2ccccc2)cc1]

to a compound

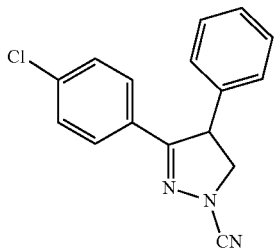 [SMILES: N#CN1CC(c2ccccc2)C(c2ccc(Cl)cc2)=N1]

Step (b): reacting the compound

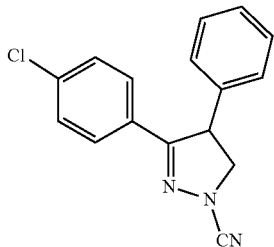 [SMILES: N#CN1CC(c2ccccc2)C(c2ccc(Cl)cc2)=N1]

with an acetimidamide agent to form a compound

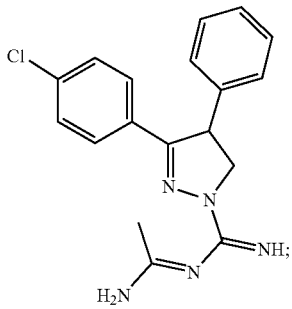 [SMILES: C/C(N)=N\C(=N)N1CC(c2ccccc2)C(c2ccc(Cl)cc2)=N1]

and

Step (c): reacting the compound

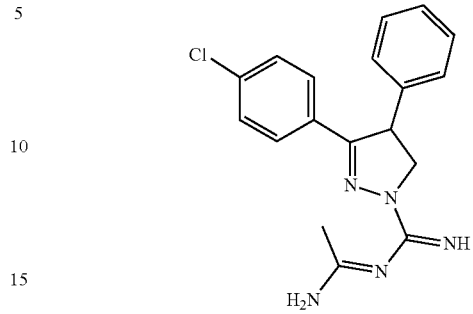

with a compound

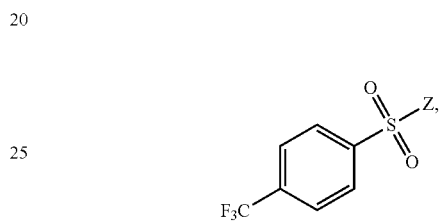

wherein Z is a third leaving group, to form (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

While the HPLC and SFC are widely used in the pharmaceutical industry for separation and purification of chiral organic molecules, in the case at hand, separation of rac-1 into enantiomers proved to be tedious, time-consuming, and costly because of the very low solubility of rac-1 in many organic solvents (solubility of rac-1 in dichloromethane is about 1 mg/mL). To overcome this obstacle, the present inventors discovered an enantioselective approach to (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide (S)-1 in high optical purity.

According to an embodiment, a process for the preparation of (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide is provided. The process includes the steps of:

providing a compound

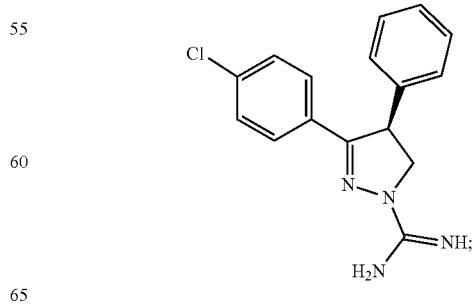

and converting the compound

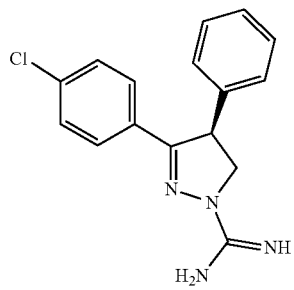 [SMILES: N=C(N)N1C[C@H](c2ccccc2)C(c2ccc(Cl)cc2)=N1]

to (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

The step of providing the compound

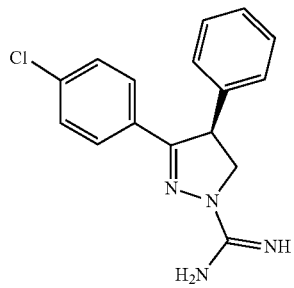 [SMILES: N=C(N)N1C[C@H](c2ccccc2)C(c2ccc(Cl)cc2)=N1]

may include:
contacting the compound

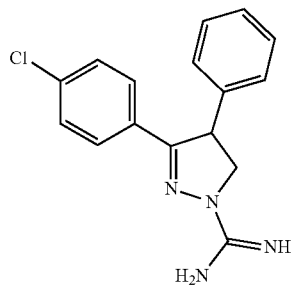 [SMILES: N=C(N)N1CC(c2ccccc2)C(c2ccc(Cl)cc2)=N1]

with an optically active isomer of an acid to form an adduct of a compound

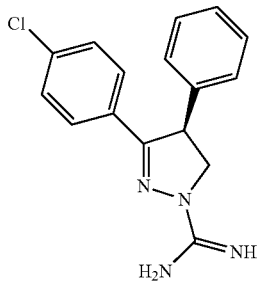 [SMILES: N=C(N)N1C[C@H](c2ccccc2)C(c2ccc(Cl)cc2)=N1]

and the optically active isomer of an acid; and converting the adduct of the compound

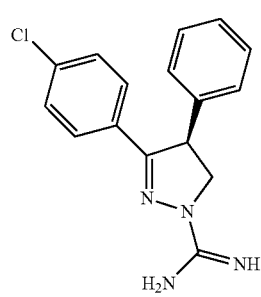 [SMILES: N=C(N)N1C[C@H](c2ccccc2)C(c2ccc(Cl)cc2)=N1]

and the optically active isomer of the acid to the compound

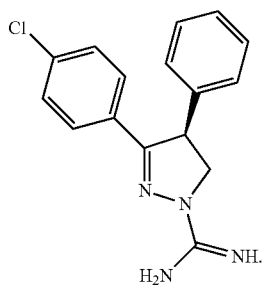 [SMILES: N=C(N)N1C[C@H](c2ccccc2)C(c2ccc(Cl)cc2)=N1]

The step of contacting the compound

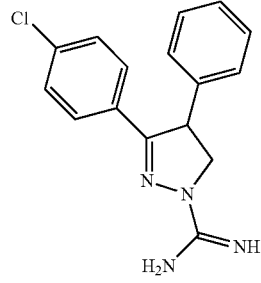 [SMILES: N=C(N)N1CC(c2ccccc2)C(c2ccc(Cl)cc2)=N1]

with the optically active isomer of the acid to form the adduct of the compound

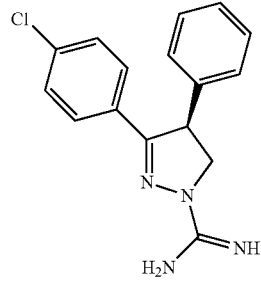 [SMILES: N=C(N)N1C[C@H](c2ccccc2)C(c2ccc(Cl)cc2)=N1]

and the optically active isomer of the acid may include:

contacting the compound

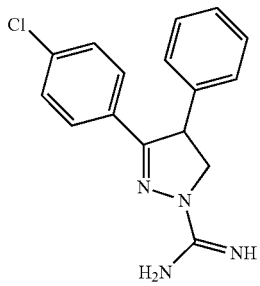 [SMILES: N=C(N)N1CC(c2ccccc2)C(c2ccc(Cl)cc2)=N1]

with the optically active isomer of the acid to form the adduct of a compound

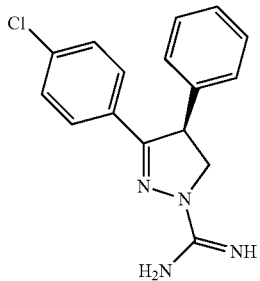 [SMILES: N=C(N)N1C[C@H](c2ccccc2)C(c2ccc(Cl)cc2)=N1]

and the optically active isomer of the acid; and
separating the adduct of the compound

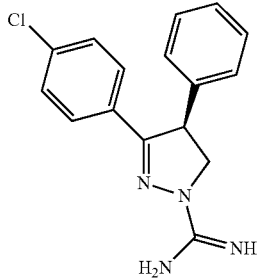 [SMILES: N=C(N)N1C[C@H](c2ccccc2)C(c2ccc(Cl)cc2)=N1]

and the optically active isomer of the acid from its enantiomer.

The step of separating the adduct of the compound

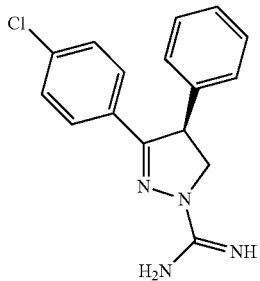 [SMILES: N=C(N)N1C[C@H](c2ccccc2)C(c2ccc(Cl)cc2)=N1]

and the optically active isomer of the acid from its enantiomer may be carried out by crystallization of the adduct of the compound

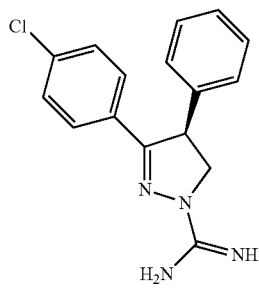 [SMILES: N=C(N)N1C[C@H](c2ccccc2)C(c2ccc(Cl)cc2)=N1]

and the optically active isomer of the acid from a solvent.

The optically active isomer of the acid may be an optically active isomer of a carboxylic acid, for example, D-aspartic acid.

A diastereomeric excess of the adduct of the compound

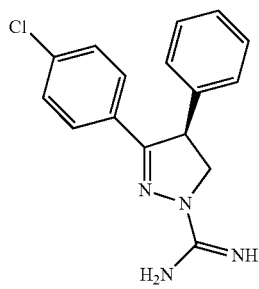 [SMILES: N=C(N)N1C[C@H](c2ccccc2)C(c2ccc(Cl)cc2)=N1]

and the optically active isomer of the acid after crystallization is greater than 95%.

The solvent may be water, an organic solvent, or a combination thereof. The organic solvent may be an individual solvent or a combination of two or more individual solvents. For example, the solvent is water, a C1 to C5 alcohol, or a combination thereof. For example, the solvent may be water, methanol, or a combination thereof.

The step of contacting the compound

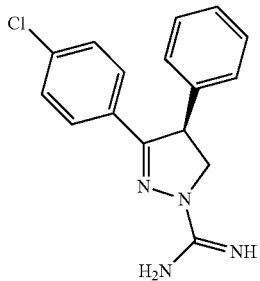 [SMILES: N=C(N)N1C[C@H](c2ccccc2)C(c2ccc(Cl)cc2)=N1]

with the optically active isomer of the acid to form the adduct of the compound

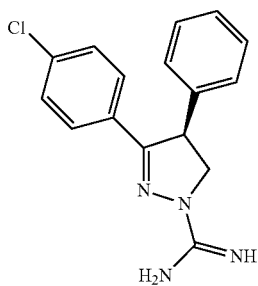 [SMILES: N=C(N)N1C[C@H](c2ccccc2)C(c2ccc(Cl)cc2)=N1]

and the optically active isomer of the acid may be preceded by:

reacting compound

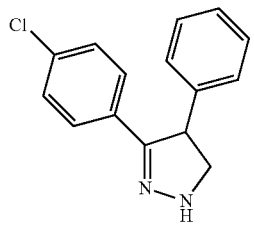

with a compound

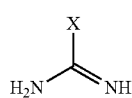

or its salt, wherein X is a first leaving group, to form the compound

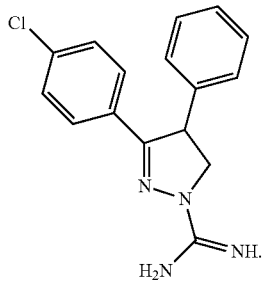 [SMILES: N=C(N)N1CC(c2ccccc2)C(c2ccc(Cl)cc2)=N1]

The first leaving group may be S—R, wherein R is a substituted or unsubstituted C1 to C10 alkyl group, a substituted or unsubstituted C3 to C10 cycloalkyl group, a substituted or unsubstituted C6 to C20 aryl group, or a substituted or unsubstituted C3 to C20 heteroaryl group.

X in the compound

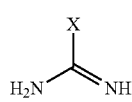

or its salt may be S—R, wherein R is a substituted or unsubstituted C1 to C10 alkyl group, a substituted or unsubstituted C3 to C10 cycloalkyl group, a substituted or unsubstituted C6 to C20 aryl group, or a substituted or unsubstituted C3 to C20 heteroaryl group. For example, R may be a substituted or unsubstituted C1 to C5 alkyl group.

The step of converting the adduct of the compound

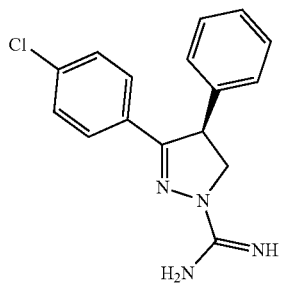 [SMILES: N=C(N)N1C[C@H](c2ccccc2)C(c2ccc(Cl)cc2)=N1]

and the optically active isomer of the acid to the compound

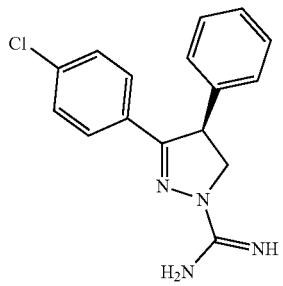 [SMILES: N=C(N)N1C[C@H](c2ccccc2)C(c2ccc(Cl)cc2)=N1]

may include:

contacting the adduct of the compound

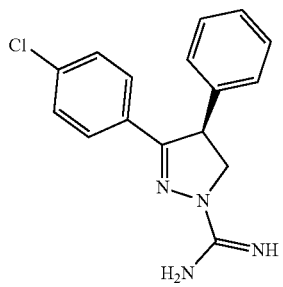 [SMILES: N=C(N)N1C[C@H](c2ccccc2)C(c2ccc(Cl)cc2)=N1]

and the optically active isomer of an acid with a base to form the compound

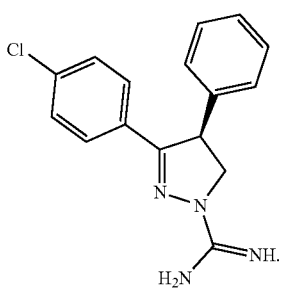 [SMILES: N=C(N)N1C[C@H](c2ccccc2)C(c2ccc(Cl)cc2)=N1]

X in the compound

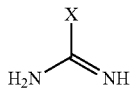

or its salt may be S—R, wherein R is a substituted or unsubstituted C1 to C10 alkyl group, a substituted or unsubstituted C3 to C10 cycloalkyl group, a substituted or unsubstituted C6 to C20 aryl group, or a substituted or unsubstituted C3 to C20 heteroaryl group. For example, R is a substituted or unsubstituted C1 to C5 alkyl group.

The step of converting the adduct of the compound

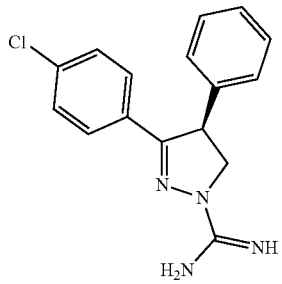 [SMILES: N=C(N)N1C[C@H](c2ccccc2)C(c2ccc(Cl)cc2)=N1]

and the optically active isomer of the acid to the compound

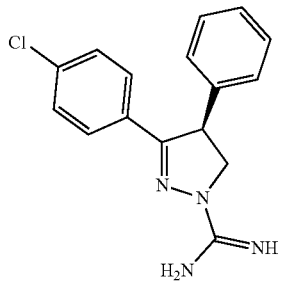 [SMILES: N=C(N)N1C[C@H](c2ccccc2)C(c2ccc(Cl)cc2)=N1]

may include:
  contacting the adduct of the compound

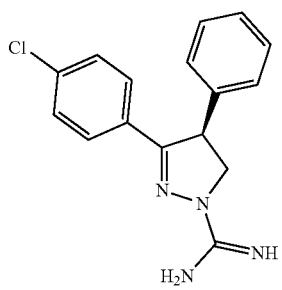 [SMILES: N=C(N)N1C[C@H](c2ccccc2)C(c2ccc(Cl)cc2)=N1]

and the optically active isomer of an acid with a base to form the compound

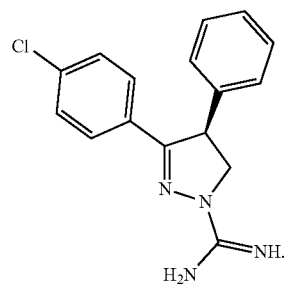 [SMILES: N=C(N)N1C[C@H](c2ccccc2)C(c2ccc(Cl)cc2)=N1]

The step of converting the compound

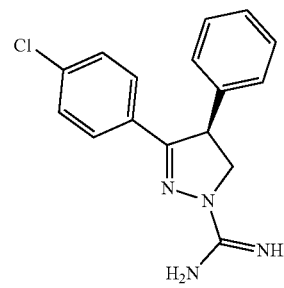 [SMILES: N=C(N)N1C[C@H](c2ccccc2)C(c2ccc(Cl)cc2)=N1]

to (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide may include:
  reacting the compound

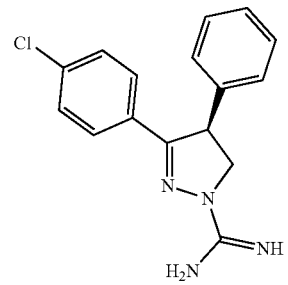 [SMILES: N=C(N)N1C[C@H](c2ccccc2)C(c2ccc(Cl)cc2)=N1]

with a compound

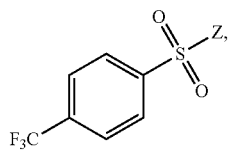

wherein Z is a third leaving group to form a compound

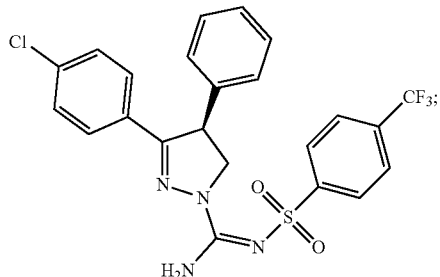

and
reacting the compound

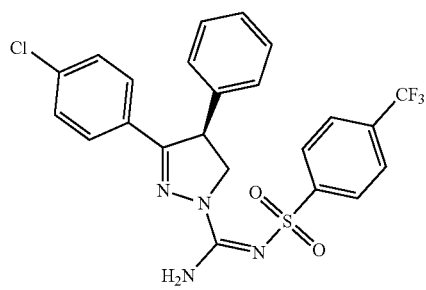 [SMILES: N/C(=N/S(=O)(=O)c1ccc(C(F)(F)F)cc1)N1C[C@H](c2ccccc2)C(c2ccc(Cl)cc2)=N1]

with a compound

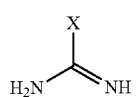

or its salt, wherein X is a first leaving group, to form (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

The step of converting the compound

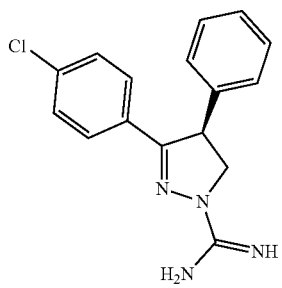 [SMILES: N=C(N)N1C[C@H](c2ccccc2)C(c2ccc(Cl)cc2)=N1]

to (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide may include:

reacting the compound

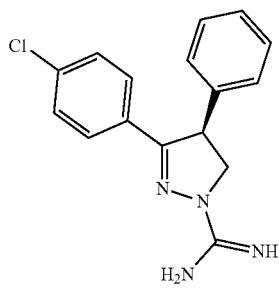 [SMILES: N=C(N)N1C[C@H](c2ccccc2)C(c2ccc(Cl)cc2)=N1]

with compound

or its salt, wherein Y is a second leaving group, to form compound

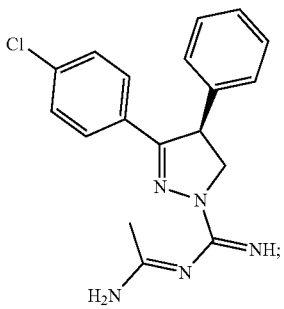 [SMILES: C/C(N)=N\C(=N)N1C[C@H](c2ccccc2)C(c2ccc(Cl)cc2)=N1]

and
reacting the compound

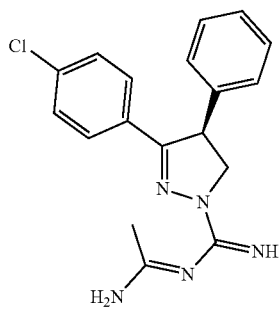 [SMILES: C/C(N)=N\C(=N)N1C[C@H](c2ccccc2)C(c2ccc(Cl)cc2)=N1]

with a compound

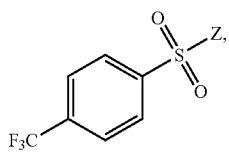

wherein Z is a third leaving group, to form (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

Y in the compound

or its salt may be X—R, wherein X is O or S, and R is a substituted or unsubstituted C1 to C10 alkyl group, a substituted or unsubstituted C3 to C10 cycloalkyl group, a substituted or unsubstituted C2 to C10 alkanoyl group, a substituted or unsubstituted C4 to C10 cycloalkanoyl group, a substituted or unsubstituted C6 to C20 aryl group, or a substituted or unsubstituted C3 to C20 heteroaryl group. For example, R may be a substituted or unsubstituted C1 to C5 alkyl group.

Z in the compound

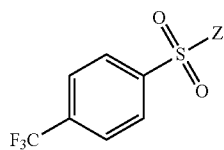

may be a halide, for example, fluoride, chloride, bromide, or iodide.

Alternatively, the step of converting the compound

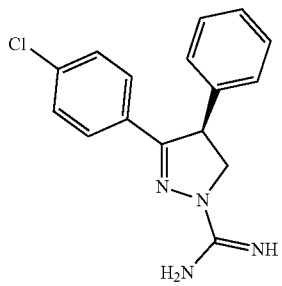 [SMILES: N=C(N)N1C[C@H](c2ccccc2)C(c2ccc(Cl)cc2)=N1]

to (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide comprises:

reacting the compound

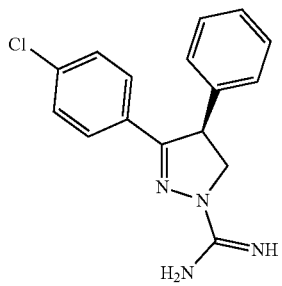 [SMILES: N=C(N)N1C[C@H](c2ccccc2)C(c2ccc(Cl)cc2)=N1]

with a compound

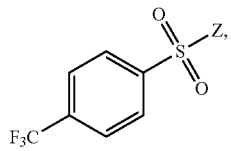

wherein Z is a leaving group to form a compound

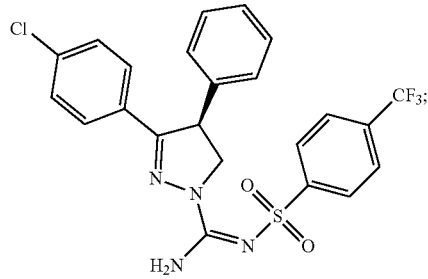 [SMILES: N/C(=N/S(=O)(=O)c1ccc(C(F)(F)F)cc1)N1C[C@H](c2ccccc2)C(c2ccc(Cl)cc2)=N1]

and
reacting the compound

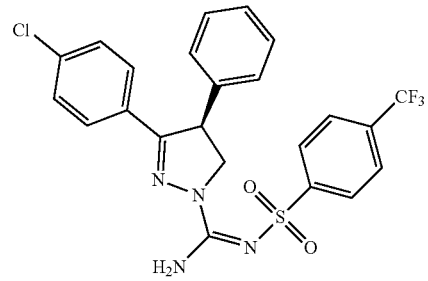 [SMILES: N/C(=N/S(=O)(=O)c1ccc(C(F)(F)F)cc1)N1C[C@H](c2ccccc2)C(c2ccc(Cl)cc2)=N1]

with a compound

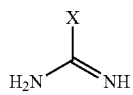

or its salt, wherein X is a first leaving group, to form (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.

(S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide may be purified by a recrystallization from an organic solvent, and a purity of (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide after the recrystallization may be greater than 98.5%. The organic solvent may be an individual solvent or a combination of two or more individual solvents.

In an embodiment, a process for the preparation of (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide is thereby provided. The process includes:

Step (a): reacting a compound

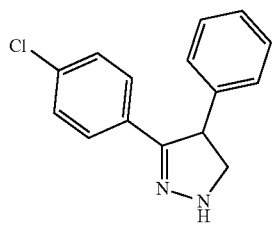 [SMILES: Clc1ccc(C2=NNCC2c2ccccc2)cc1]

with a compound

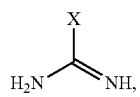

wherein X is a first leaving group, to form a compound

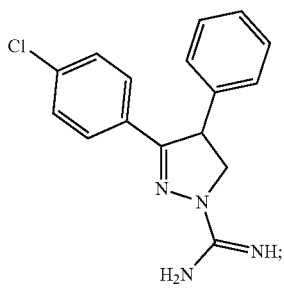 [SMILES: N=C(N)N1CC(c2ccccc2)C(c2ccc(Cl)cc2)=N1]

Step (b): contacting the compound

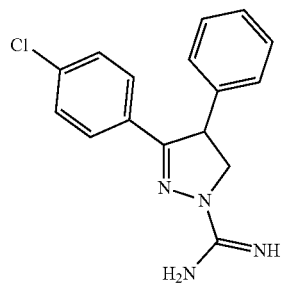

with an optically active isomer of an acid to form an adduct of a compound

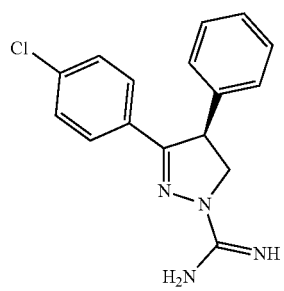 [SMILES: N=C(N)N1C[C@H](c2ccccc2)C(c2ccc(Cl)cc2)=N1]

and an acid salt;

Step (c): separating the adduct of the compound

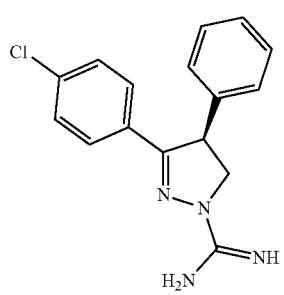 [SMILES: N=C(N)N1C[C@H](c2ccccc2)C(c2ccc(Cl)cc2)=N1]

and the optically active isomer of the acid from its enantiomer;

Step (d): contacting the adduct of the compound

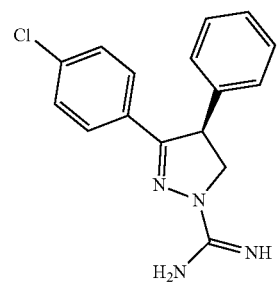 [SMILES: N=C(N)N1C[C@H](c2ccccc2)C(c2ccc(Cl)cc2)=N1]

and the optically active isomer of the acid with a base to form compound

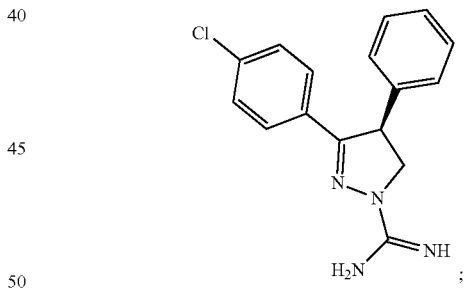

Step (e): reacting the compound with compound
wherein Y is a second leaving group, to form compound
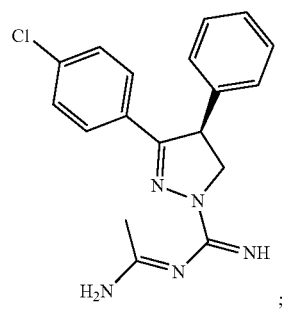 [SMILES: C/C(N)=N\C(=N)N1C[C@H](c2ccccc2)C(c2ccc(Cl)cc2)=N1]
Step (f): reacting the compound
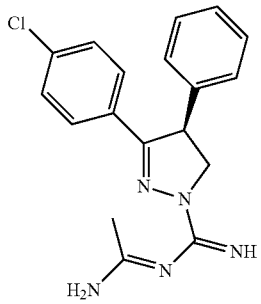 [SMILES: C/C(N)=N\C(=N)N1C[C@H](c2ccccc2)C(c2ccc(Cl)cc2)=N1]
with compound
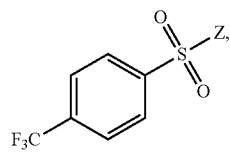
wherein Z is a third leaving group, to form (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide.
An exemplary approach is shown in Scheme 4 below.
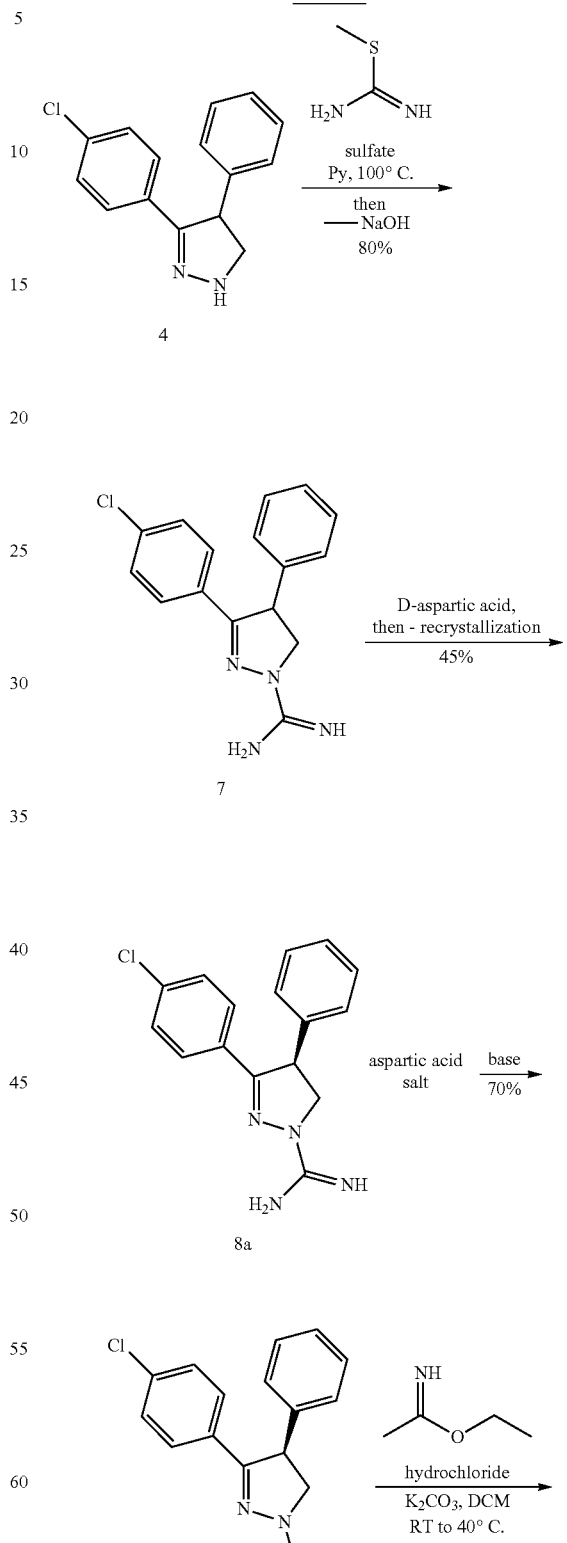

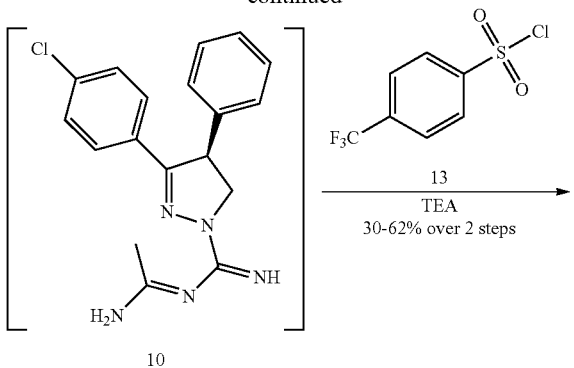

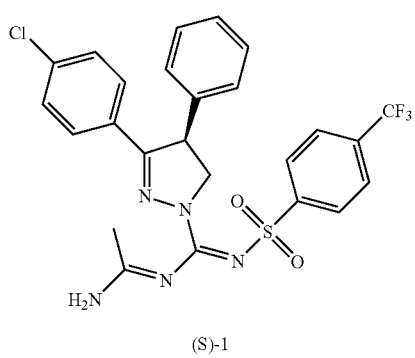

In Step (a), the 4,5-dihydro-1H-pyrazole derivative 4 may be reacted with a compound

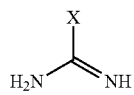

(wherein X is a leaving group), such as S-methylisothiourea to give cyclic urea derivative 7 in 80% yield.

In Step (b), the cyclic urea derivative 7 may be treated with an optically active isomer of an acid, which may be any acid having at least one element of chirality. In an embodiment, the acid may be a carboxylic acid or a sulfonic acid. The acid may have one or more acid residues. For example, the carboxylic acid may be a monocarboxylic acid, a dicarboxylic acid, a tricarboxylic acid, or a tetracarboxylic acid, but is not limited thereto. Also, the sulfonic acid may be a monosulfonic acid, a disulfonic acid, a trisulfonic acid, or a tetrasulfonic acid, but is not limited thereto. In an embodiment, the acid may be a D-aspartic acid. Accordingly, the cyclic urea derivative 7 may be treated with an optically active isomer of a carboxylic acid, for example, D-aspartic acid, in a certain solvent, for example, methanol, to give a D-aspartate salt 8a with diastereomeric excess (de) of greater than 95% after crystallization. The acid salt usually crystallizes out of the solution in high purity and the diastereomeric excess (de) of 95.0% to 98.5%. The desired diastereomer may be further enriched by an additional recrystallization or reslurrying to achieve the diastereomeric excess (de) of 99% or greater.

In Step (c), the resulting salt can be basified with a base under appropriate conditions to give the desired enantiomer 9 in a 35% yield (the theoretical maximum yield of 50%) with a retention of chirality.

In Step (d), the desired enantiomer 9 is treated with acetimidamide, for example, ethyl acetimidamide (which may be obtained by basifying ethyl acetimidamide hydrochloride salt), in an appropriate non-polar solvent (for example, dichloromethane) at room temperature, followed by stirring at 40° C. to give compound 10, which may be used in the next step without purification.

The compound 10 may be then treated with the compound

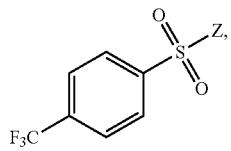

wherein Z is a leaving group, for example, with 4-(trifluoromethyl)benzenesulfonyl chloride 13 in the presence of an organic base, such as DIPEA to yield crude (S)-MRI-1867. The crude material may be recrystallized from an organic solvent. The organic solvent may be a non-alcohol solvent. In an embodiment, the crude material may be recrystallized from a non-alcohol solvent, such as methyl tert-butyl ether (MTBE) and ethyl acetate to provide (S)-MRI-1867 with enantiomeric excess of 95% or greater and HPLC purity of 98.5% or greater.

It is understood that racemic MRI-1867 can be obtained via the sequence shown in Scheme 4 without a need for conversion of the cyclic urea derivative 7 to the mixture of the diastereomeric salts, separation of the diastereomeric salts, and basification. Instead, the cyclic urea derivative 7 is directly treated with acetimidamide to produce compound 10, which is then reacted with 4-(trifluoromethyl)benzenesulfonyl chloride 13 to provide racemic MRI-1867.

The enantiomer 9 and the racemic compound 14 can be respectively converted to (S)-MRI-1867 ((S)-1) and racemic MRI-1867 (rac-1) by first reacting with 4-(trifluoromethyl)benzenesulfonyl chloride 13 followed by treatment with acetimidamide (Scheme 5) via intermediates 15 and 16, respectively:

Scheme 5
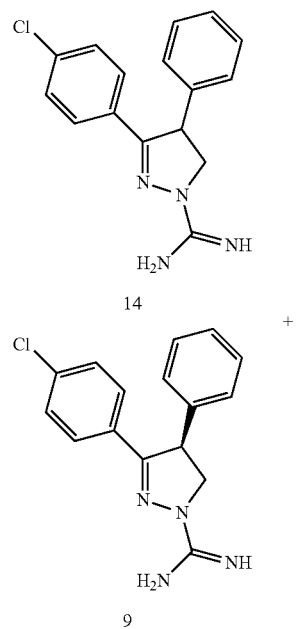
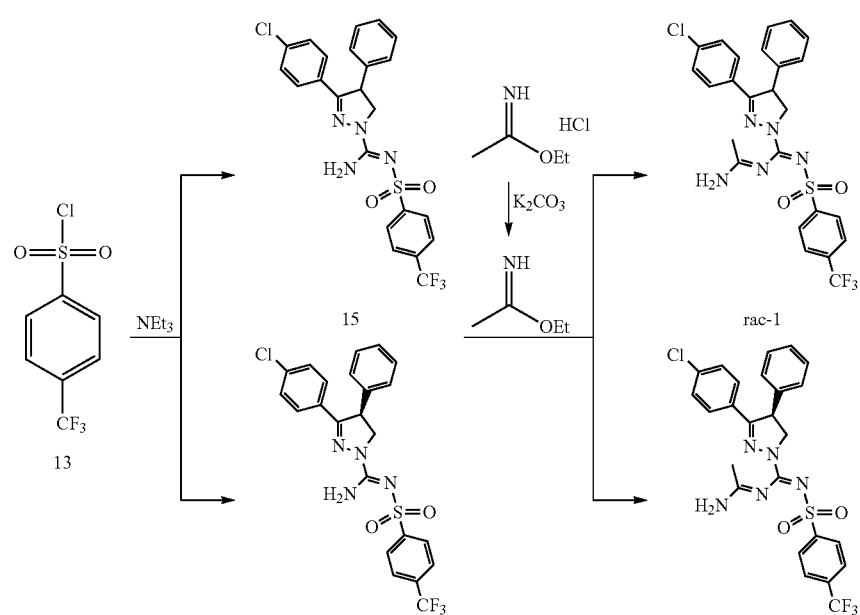

In another embodiment, a compound represented by one of the following formulae or its enantiomer is provided:

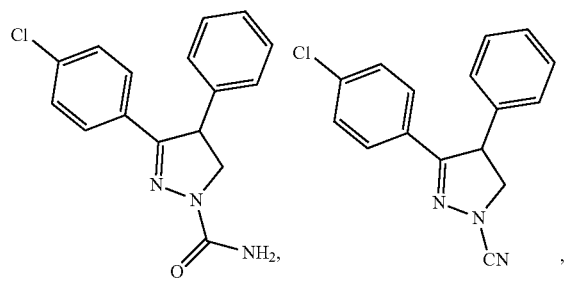

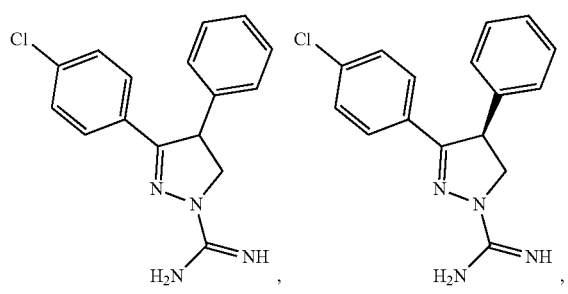

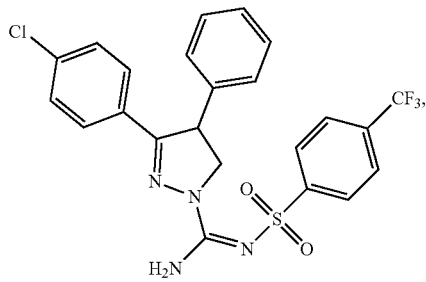

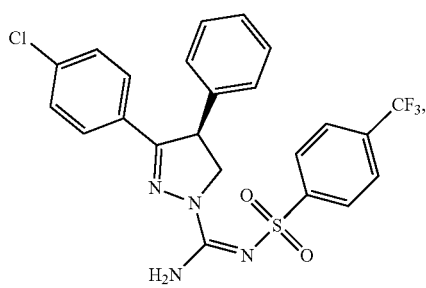

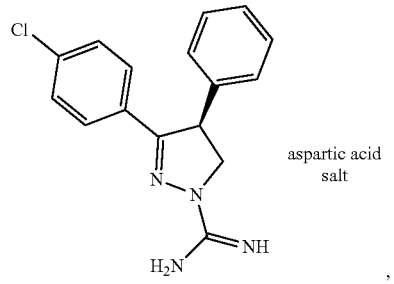

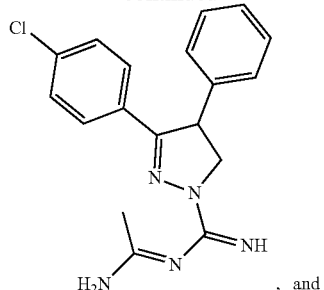

, and

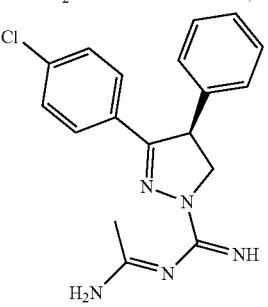

.

The present invention is illustrated and further described in more detail with reference to the following non-limiting examples.

EXAMPLES

Preparation of (1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide (Rac-1) According to Scheme 2

Ethyl ((4-(trifluoromethyl)phenyl)sulfonyl)carbamate (3b)

4-(Trifluoromethyl)benzenesulfonamide (2, 165 g, 733 mmol, 1.0 equiv) was dissolved in THF (1,000 mL) followed by the addition of triethylamine (306 mL, 2,198 mmol, 3.0 equiv). The reaction was cooled to 0-4° C. with ice-bath, and ethyl chloroformate (84 mL, 879 mmol, 1.2 equiv) was added in 30 min to keep internal temperature below 20° C. The reaction was stirred at room temperature overnight, filtered, and washed with THF (200 mL). The filtrate was concentrated and the residue was treated with saturated aqueous $Na_2CO_3$ solution (270 mL), filtered, and extracted with EtOAc (2×200 mL). The aqueous layer was then acidified with 6 N HCl to pH=2-3, and extracted with DCM (3×200 mL). The organic layer was washed with water (3×200 mL), brine (2×200 mL), dried over $Na_2SO_4$, filtered, and concentrated to give ethyl ((4-(trifluoromethyl)phenyl)sulfonyl)carbamate (3b, 190 g, 639 mmol, 87% yield) as a thick oil which was solidified with standby to become a white solid.

$^1$H NMR (400 MHz, Chloroform-d) δ 8.25-8.12 (m, 2H), 7.89-7.71 (m, 2H), 7.46 (s, 1H), 4.22-4.10 (m, 2H), 1.29-1.17 (m, 3H).

m/z: 298.0 (M+H$^+$).

3-(4-Chlorophenyl)-4-phenyl-N-((4-(trifluoromethyl)phenyl)sulfonyl)-4,5-dihydro-1H-pyrazole-1-carboxamide (5)

Ethyl ((4-(trifluoromethyl)phenyl)sulfonyl)carbamate (3b, 101 g, 339 mmol, 1.05 equiv) and 3-(4-chlorophenyl)-

4-phenyl-4,5-dihydro-1H-pyrazole (4, 83 g, 323 mmol, 1.0 equiv) was suspended in toluene (850 ml), heated to 98° C. (internal), and stirred overnight at which time the reaction mixture became a brown solution and LC-MS analysis showed no pyrazole left. The reaction was cooled to room temperature followed by the addition of heptanes (1.7 L), and stirred for 3 hour. The resulting suspension was filtered, and the solid was washed with a solution of toluene and heptanes (1:3) (3×300 mL) and heptanes (400 mL). The solid was dried in air overnight, and then in vacuum oven at 40° C. overnight to give 3-(4-chlorophenyl)-4-phenyl-N-((4-(trifluoromethyl)phenyl)sulfonyl)-4,5-dihydro-1H-pyrazole-1-carboxamide (5, 141.4 g, 278 mmol, 86% yield) as an off white solid.

(E)-3-(4-chlorophenyl)-4-phenyl-N-((4-(trifluoromethyl)phenyl)sulfonyl)-4,5-dihydro-1H-pyrazole-1-carbimidoyl chloride (6)

3-(4-chlorophenyl)-4-phenyl-N-((4-(trifluoromethyl)phenyl)sulfonyl)-4,5-dihydro-1H-pyrazole-1-carboxamide (5, 106 g, 209 mmol, 1.0 equiv) was suspended in toluene (850 ml) followed by the addition of N-ethyl-N-isopropylpropan-2-amine (47.4 ml, 271 mmol, 1.3 equiv) (temperature rise from 20.5 to 22.6 C was observed). The mixture was stirred for 1 h to form a clear solution and then degassed by passing through a $N_2$ stream for 10 min. A solution of phosphoryl trichloride (25.3 ml, 271 mmol, 1.3 equiv) was then added in 10 min (temperature increased from 22.5 to 26.5° C.). The reaction was stirred for 15 min, heated to 95° C. (internal) for 6 hour, concentrated to dryness, and chased with toluene (2×50 mL) to get a yellow solid (6) which was used in next step directly.

(Z)—N-((E)-1-aminoethylidene)-3-(4-chlorophenyl)-4-phenyl-N'-((4-(trifluoromethyl)phenyl)sulfonyl)-4,5-dihydro-1H-pyrazole-1-carboximidamide (Rac-1)

In a flask, acetimidamide hydrochloride (39.5 g, 417 mmol, 2 equiv) was added to 2-propanol (600 ml) and then N-ethyl-N-isopropylpropan-2-amine (146 ml, 835 mmol, 4 equiv) was added. The mixture was stirred for 3 hours to get a clear solution. The yellow solid from the previous step was dissolved in DCM (1,000 mL) and cooled to −25° C. (internal) with ice-CaCl$_2$) bath, followed by the addition of above acetimidamide solution in 15 min (inner temperature did not rise significantly). The mixture was then slowly warmed to room temperature and stirred overnight. LC-MS analysis showed a process purity of 76% at 220 nm, 86% at 254 nm. The reaction was quenched with water 1,000 mL, and stirred for 1 hour. The aqueous layer was separated. The organic layer was washed with water (2×600 mL), saturated aqueous NaHCO$_3$ solution (80 mL), and brine (300 mL). The cloudy organic layer was filtered to give (Z)—N-((E)-1-aminoethylidene)-3-(4-chlorophenyl)-4-phenyl-N'-((4-(trifluoromethyl)phenyl)sulfonyl)-4,5-dihydro-1H-pyrazole-1-carboximidamide (rac-1, 30 g), and the filtrate was dried with Na$_2$SO$_4$ and concentrated. The resulting residue was treated with DCM (200 mL) and stirred for 6 h, and filtered, washed with DCM (80 mL) to give another (Z)—N-((E)-1-aminoethylidene)-3-(4-chlorophenyl)-4-phenyl-N'-((4-(trifluoromethyl)phenyl)sulfonyl)-4,5-dihydro-1H-pyrazole-1-carboximidamide (rac-1, 55 g). The solid was combined and dried in vacuum oven at 40° C. overnight to give (Z)—N-((E)-1-aminoethylidene)-3-(4-chlorophenyl)-4-phenyl-N'-((4-(trifluoromethyl)phenyl)sulfonyl)-4,5-dihydro-1H-pyrazole-1-carboximidamide (rac-1, 77 g, 68% yield) as a white solid with HPLC purity over 99%.

$^1$H NMR (400 MHz, DMSO-d$_6$) δ 7.94 (d, J=8.1 Hz, 2H), 7.81 (d, J=8.2 Hz, 2H), 7.53 (d, J=8.2 Hz, 2H), 7.38 (d, J=8.4 Hz, 3H), 7.28 (t, J=7.5 Hz, 2H), 7.25-7.09 (m, 4H), 5.09-4.93 (m, 1H), 4.43 (t, J=11.8 Hz, 1H), 3.83 (d, J=12.3 Hz, 1H), 1.75 (s, 3H).

$^{13}$C NMR (101 MHz, DMSO) δ 161.00, 158.95, 158.83, 148.11, 140.67, 135.33, 131.48, 131.16, 129.69, 129.51, 129.34, 129.12, 128.42, 127.97, 127.78, 125.80, 125.77, 125.63, 122.92, 56.81, 50.11, 20.73.

$^{19}$F NMR (376 MHz, DMSO) δ −61.37.

m/z: 547.9 (M+H$^+$).

Preparation of (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide According to Scheme 3

3-(4-chlorophenyl)-4-phenyl-4,5-dihydro-1H-pyrazole-1-carboxamide (7)

3-(4-Chlorophenyl)-4-phenyl-4,5-dihydro-1H-pyrazole (4, 5 g, 19.48 mmol, 1.0 equiv) was dissolved in THF (60 ml) followed by the addition of isocyanatotrimethylsilane (3.89 ml, 29.2 mmol, 1.5 equiv). The reaction was stirred for 24 hours and methanol (30 mL) was added, and stirred for another 4 hour. The reaction was concentrated, methanol (30 mL) was added, and the reaction mixture was stirred for 1 h. The reaction mixture was filtered and washed with methanol (30 mL), dried to give 3-(4-chlorophenyl)-4-phenyl-4,5-dihydro-1H-pyrazole-1-carboxamide (7, 4 g, 13.34 mmol, 68.5% yield) as a yellow solid.

$^1$H NMR (400 MHz, Chloroform-d) δ 7.58-7.44 (m, 2H), 7.29 (dd, J=8.1, 6.5 Hz, 2H), 7.23 (dd, J=8.1, 6.5 Hz, 4H), 7.20-7.12 (m, 2H), 5.40 (s, 1H), 4.67 (dd, J=11.8, 5.4 Hz, 1H), 4.36 (t, J=11.5 Hz, 1H), 3.99 (dd, J=11.2, 5.4 Hz, 1H). m/z: 300.1 (M+H$^+$).

3-(4-chlorophenyl)-4-phenyl-4,5-dihydro-1H-pyrazole-1-carbonitrile (11)

3-(4-chlorophenyl)-4-phenyl-4,5-dihydro-1H-pyrazole-1-carboxamide (7, 1.06 g, 3.54 mmol, 1.0 equiv) was dissolved in pyridine (30 mL) followed by the addition of tosyl chloride (2.022 g, 10.61 mmol), and the reaction was stirred for overnight. LC-MS analysis showed the reaction was complete. The reaction was quenched with water (120 mL) with ice-bath, filtered, washed with water (50 mL), and dried. 3-(4-Chlorophenyl)-4-phenyl-4,5-dihydro-1H-pyrazole-1-carbonitrile (11, 0.97 g, 3.44 mmol, 97% yield) as an off-white solid.

$^1$H NMR (400 MHz, DMSO-d$_6$) δ 7.84-7.72 (m, 2H), 7.51-7.38 (m, 2H), 7.34-7.26 (m, 2H), 7.26-7.19 (m, 1H), 7.19-7.10 (m, 2H), 5.05 (dd, J=11.0, 4.4 Hz, 1H), 4.25 (m, 1H), 3.80 (dd, J=9.7, 4.4 Hz, 1H).

m/z: 282.1 (M+H$^+$).

(E)-N-(1-aminoethylidene)-3-(4-chlorophenyl)-4-phenyl-4,5-dihydro-1H-pyrazole-1-carboximidamide (12)

Acetimidamide, HCl salt (121 mg, 1.278 mmol, 3 equiv) was added to DMF (4 ml) followed by the addition of DIPEA (0.298 ml, 1.704 mmol, 4 equiv) and stirred for 15 min to form a clear solution. To this mixture, 3-(4-chlorophenyl)-4-phenyl-4,5-dihydro-1H-pyrazole-1-carbonitrile (11, 120 mg, 0.426 mmol, 1.0 equiv) was added. The reaction was stirred at room temperature overnight, LC-MS analysis showed a 50% conversion. The reaction was then heated to 60° C., LC-MS analysis showed 75% conversion after 3 hour, and >90% conversion after another 3 hours. The reaction was concentrated under reduced pressure under 45° C., and dried under vacuum overnight to give crude (E)-N-(1-aminoethylidene)-3-(4-chlorophenyl)-4-phenyl-4,5-dihydro-1H-pyrazole-1-carboximidamide (12, 130 mg) which was used directly in next step.

m/z: 340.1 (M+H$^+$).

(Z)—N-((E)-1-aminoethylidene)-3-(4-chlorophenyl)-4-phenyl-N'-((4-(trifluoromethyl)phenyl)sulfonyl)-4,5-dihydro-1H-pyrazole-1-carboximidamide (Rac-1)

(E)-N-(1-aminoethylidene)-3-(4-chlorophenyl)-4-phenyl-4,5-dihydro-1H-pyrazole-1-carboximidamide (12, 130 mg, 0.383 mmol, 1.0 equiv) in DMF (5 mL) was added 4-(trifluoromethyl)benzenesulfonyl chloride (13, 94 mg, 0.383 mmol, 1.0 equiv) and DIPEA (134 μl, 0.765 mmol, 2.0 equiv). The reaction was stirred at room temperature for 30 min. LC-MS analysis showed 60% conversion, and no progress in a longer time. The reaction was concentrated and the residue was purified by silica gel flash chromatography eluting with 0-5% MeOH in DCM to give (E)-N-((E)-1-aminoethylidene)-3-(4-chlorophenyl)-4-phenyl-N'-((4-(trifluoromethyl)phenyl)sulfonyl)-4,5-dihydro-1H-pyrazole-1-carboximidamide (rac-1, 110 mg, 0.201 mmol, 52.5% yield) as a white solid.

Preparation of (S,1E,NE)-N-(1-aminoethylidene)-3-(4-chlorophenyl)-4-phenyl-N'-((4-(trifluoromethyl)phenyl)sulfonyl)-4,5-dihydro-1H-pyrazole-1-carboximidamide According to Scheme 4

3-(4-chlorophenyl)-4-phenyl-4,5-dihydro-1H-pyrazole-1-carboximidamide (7)

3-(4-chlorophenyl)-4-phenyl-4,5-dihydro-1H-pyrazole (2, 390.5 g, 1521 mmol, 1.0 equiv) was added to pyridine (1,400 mL) followed by the addition of methyl carbamimidothioate, sulfuric acid (237 g, 852 mmol, 0.56 equiv). The mixture was vacuumed and then purged with nitrogen for 2 times, heated to 105° C. (from 20° C. in 25 min), and stirred for 48 hours. LC-MS analysis showed the reaction was completed. The reaction was then cooled to room temperature. MTBE (4.2 L) was added, and the reaction was stirred overnight. The solid was filtered and washed with MTBE (1 L). The solid was suspended in methanol (1.4 L), and basified with 5 N NaOH (350 mL, 1750 mmol, 1.15 equiv) followed by the addition of water (5 L), and stirred for 3 h. The resulting solid was filtered, washed with water (800 mL×3) until the pH of washout water around 8-9, and dried in air overnight. The solid was suspended in MTBE (1.5 L) and stirred for 2 h, filtered, and washed with MTBE (200 mL), dried in vacuum oven for 2 day at 45° C. to give 3-(4-chlorophenyl)-4-phenyl-4,5-dihydro-1H-pyrazole-1-carboximidamide (7, 353 g, 1181 mmol, 78% yield) as an light yellow solid.

$^1$H NMR (400 MHz, DMSO-d$_6$) δ 7.73-7.62 (m, 2H), 7.43-7.35 (m, 2H), 7.30 (t, J=7.5 Hz, 2H), 7.25-7.16 (m, 3H), 6.64 (s, 3H), 5.00 (dd, J=11.4, 4.6 Hz, 1H), 4.25 (t, J=11.2 Hz, 1H), 3.81 (dd, J=10.9, 4.7 Hz, 1H).

$^{13}$C NMR (101 MHz, DMSO) δ 151.31, 141.57, 133.75, 130.70, 129.53, 129.00, 128.45, 127.67, 127.65, 56.69, 50.07.

m/z: 299.0 (M+H$^+$).

(S)-3-(4-chlorophenyl)-4-phenyl-4,5-dihydro-1H-pyrazole-1-carboximidamide aspartate (8)

3-(4-chlorophenyl)-4-phenyl-4,5-dihydro-1H-pyrazole-1-carboximidamide (7, 398.1 g, 1,332 mmol) suspended in a mixture solution of MeOH (9,000 mL), and D-aspartic acid (177 g, 1,332 mmol) was added. The reaction was heated to 60° C. (the reaction became almost clear in 5 min and then became cloudy after 15 min), and stirred for 1 h at 60° C. The reaction was cooled to room temperature and stirred overnight (20 h). The reaction was filtered and washed with methanol (2×100 mL). The solid was dried in air overnight, and then dried under vacuum to give (S)-3-(4-chlorophenyl)-4-phenyl-4,5-dihydro-1H-pyrazole-1-carboximidamide, D-aspartic acid (8a, 231.7 g, 536 mmol, 40.3% yield) as a white solid with 95.7% ee.

Re-slurry: (S)-3-(4-chlorophenyl)-4-phenyl-4,5-dihydro-1H-pyrazole-1-carboximidamide, D-aspartic (8a, 254 g, 588 mmol) (95.7% ee) was suspended in 30% water in MeOH (2.5 L) and heated to 64° C. for 1.5 hour. The suspension was cooled with ice-bath and stirred over 3 hrs and filtered to give (S)-3-(4-chlorophenyl)-4-phenyl-4,5-dihydro-1H-pyrazole-1-carboximidamide, D-aspartic acid (8a, 214 g, 496 mmol, 84% yield) as a white solid with >99% ee. The filtrate (with 73% ee) was concentrated to −250 mL followed by the addition of methanol (100 mL). The mixture was stirred overnight at room temperature and the resulting solid was filtered and washed with methanol (200 mL), dried under vacuum to give another 25 g of 8a as a white solid with >99% ee. (Overall, 239 g of 8a was obtained with 94% yield).

$^1$H NMR (400 MHz, Methanol-d$_4$) δ 7.77-7.68 (m, 2H), 7.39-7.19 (m, 7H), 5.17 (dd, J=11.3, 5.1 Hz, 1H), 4.49 (dd, J=11.3, 10.4 Hz, 1H), 3.96 (dd, J=10.4, 5.1 Hz, 1H), 3.71 (dd, J=10.7, 3.4 Hz, 1H), 3.34 (s, 3H), 2.85 (dd, J=17.3, 3.4 Hz, 1H), 2.54 (dd, J=17.3, 10.7 Hz, 1H).

$^{13}$C NMR (101 MHz, CD$_3$OD) δ 176.76, 173.18, 159.88, 153.83, 139.02, 136.61, 129.32, 129.22, 128.62, 127.98, 127.96, 127.12, 55.02, 52.61, 52.04, 36.34.

m/z: 299.0 (M+H$^+$).

(S)-3-(4-chlorophenyl)-4-phenyl-4,5-dihydro-1H-pyrazole-1-carboximidamide (9)

(S)-3-(4-chlorophenyl)-4-phenyl-4,5-dihydro-1H-pyrazole-1-carboximidamide, D-aspartic acid (8a, 50 g, 116 mmol) was suspended in water (1,300 mL) and stirred for 30 min. To this suspension, 5 M ammonium hydroxide (46.3 mL, 232 mmol) was added slowly in 1 hour keeping the pH of the mixture below 9.7. The mixture was stirred for another 1 h after addition, at which time pH of reaction went to 9.5. The solid was filtered and washed with water (300 ml) until pH=8, and then dried under vacuum to give (S)-3-(4-chlorophenyl)-4-phenyl-4,5-dihydro-1H-pyrazole-1-carboximidamide (9, 30 g, 100 mmol, 87% yield) as an off-white solid with 97.6% ee.

$^1$H NMR (400 MHz, DMSO-d$_6$) δ 7.73-7.62 (m, 2H), 7.43-7.35 (m, 2H), 7.30 (t, J=7.5 Hz, 2H), 7.25-7.16 (m, 3H), 6.64 (s, 3H), 5.00 (dd, J=11.4, 4.6 Hz, 1H), 4.25 (t, J=11.2 Hz, 1H), 3.81 (dd, J=10.9, 4.7 Hz, 1H).

¹³C NMR (101 MHz, DMSO) δ 151.31, 141.57, 133.75, 130.70, 129.53, 129.00, 128.45, 127.67, 127.65, 56.69, 50.07.

m/z: 299.0 (M+H⁺).

(S,E)-N-(1-aminoethylidene)-3-(4-chlorophenyl)-4-phenyl-4,5-dihydro-1H-pyrazole-1-carboximidamide (10)

DCM (200 mL) was added to a 500 mL 4-neck flask equipped with overhead stirrer, and degassed by passing through a stream of N₂ for 15 min followed by the addition of (S)-3-(4-chlorophenyl)-4-phenyl-4,5-dihydro-1H-pyrazole-1-carboximidamide (9, 10 g, 33.5 mmol, 1.0 equiv). In a separate flask, ethyl acetamidate HCl salt (20.68 g, 167 mmol, 5 equiv) was suspended in an aqueous 3 M K₂CO₃ solution (112 mL, 335 mmol, 10 equiv) and stirred for 5 min followed by the addition of DCM (100 mL). The reaction mixture was then stirred for another 10 min. The organic phase was separated, dried with Na₂SO₄, filtered, and washed with DCM (30 mL). The filtrate was added to the previously mentioned 4-neck flask. The reaction was heated to 35° C. (outside, internal temp at 31.0-31.9° C.) and stirred for 4 days, at which time LC-MS analysis showed >94% conversion. The reaction was cooled to room temperature, filtered through a pad of celite, and washed with DCM (50 mL). The filtrate was concentrated under reduced pressure at (35° C.) to give crude (S,E)-N-(1-aminoethylidene)-3-(4-chlorophenyl)-4-phenyl-4,5-dihydro-1H-pyrazole-1-carboximidamide (10, 11.1 g, 32.7 mmol, 98% yield) as a yellow solid.

¹H NMR (400 MHz, DMSO-d₆) δ 10.70 (s, 1H), 8.14 (s, 1H), 7.67-7.58 (m, 2H), 7.39-7.32 (m, 2H), 7.32-7.23 (m, 2H), 7.23-7.09 (m, 3H), 4.85 (dd, J=11.4, 4.4 Hz, 1H), 4.23 (t, J=11.4 Hz, 1H), 3.95-3.84 (m, 1H), 1.88 (s, 3H).

¹³C NMR (101 MHz, DMSO) δ 159.89, 153.01, 141.48, 133.95, 130.69, 129.66, 129.51, 129.26, 129.09, 128.49, 127.67, 127.64, 127.54, 57.26, 50.09, 49.36, 25.00.

m/z: 340.0 (M+H⁺).

(S,E)-N-((E)-1-aminoethylidene)-3-(4-chlorophenyl)-4-phenyl-N'-((4-(trifluoromethyl)phenyl)sulfonyl)-4,5-dihydro-1H-pyrazole-1-carboximidamide ((S)-1)

(S,E)-N-(1-aminoethylidene)-3-(4-chlorophenyl)-4-phenyl-4,5-dihydro-1H-pyrazole-1-carboximidamide (10, 11.1 g, 32.7 mmol) was dissolved in DCM (156 ml) and cooled with ice-bath. 4-(Trifluoromethyl)benzenesulfonyl chloride (10.79 g, 44.1 mmol, 1.35 equiv) was added followed by the addition of triethylamine (6.15 ml, 44.1 mmol, 1.35 equiv) in 30 sec. The reaction stirred for 30 min at 0-4° C., and then room temperature overnight, at which time LC-MS analysis showed no starting material left. The reaction mixture (a suspension) was filtered and the solid was washed with DCM (50 mL). The filtrate was washed with water (100 mL×3), dried over Na₂SO₄, and filtered. The filtrate was concentrated to give 20 g residue, which was dissolved in MTBE (100 mL) and stirred for 3-4 hours. The solid was filtered and washed with MTBE (50 mL) and dried under vacuum to give (S)-1 (9.8 g, 55% yield) as a white solid with >99% ee.

¹H NMR (400 MHz, DMSO-d₆) δ 8.03-7.91 (m, 2H), 7.84 (d, J=8.4 Hz, 2H), 7.55 (d, J=8.3 Hz, 2H), 7.50-7.37 (m, 3H), 7.37-7.28 (m, 2H), 7.28-7.13 (m, 4H), 5.04 (dd, J=11.3, 4.8 Hz, 1H), 4.46 (t, J=11.8 Hz, 1H), 3.86 (dd, J=12.2, 4.7 Hz, 1H), 1.77 (s, 3H).

¹³C NMR (101 MHz, DMSO) δ 161.00, 158.95, 158.83, 148.11, 140.67, 135.33, 131.48, 131.16, 129.69, 129.51, 129.34, 129.12, 128.42, 127.97, 127.78, 125.80, 125.77, 125.63, 122.92, 56.81, 50.11, 20.73.

m/z: 547.9 (M+H⁺).

It should be understood that the embodiments described in the examples should be considered in a descriptive sense only and not for purposes of limitation. Descriptions of features or aspects within each embodiment should typically be considered as available for other similar features or aspects in other embodiments.

While one or more embodiments of the present disclosure have been described, it will be understood by those of ordinary skill in the art that various changes in form and details may be made therein without departing from the spirit and scope of the present disclosure as defined by the following claims.

What is claimed is:

1. A process for the preparation of (S,1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide, comprising the steps of:

providing a compound

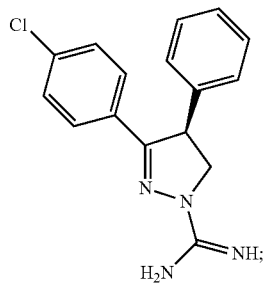 [SMILES: N=C(N)N1C[C@H](c2ccccc2)C(c2ccc(Cl)cc2)=N1]

and converting the compound

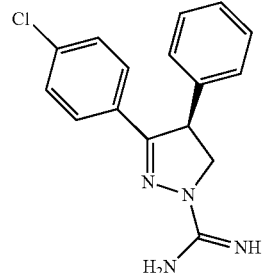

to (S,1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide;

wherein the step of providing the compound

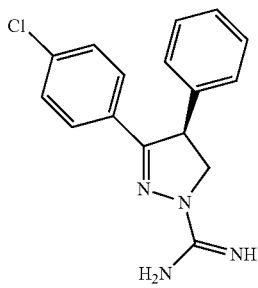 [SMILES: N=C(N)N1C[C@H](c2ccccc2)C(c2ccc(Cl)cc2)=N1]

comprises:
contacting the compound

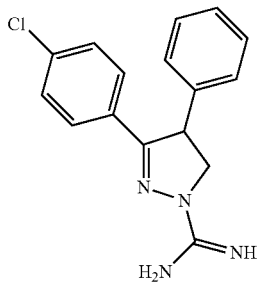 [SMILES: N=C(N)N1CC(c2ccccc2)C(c2ccc(Cl)cc2)=N1]

with an optically active isomer of an acid to form an adduct of a compound

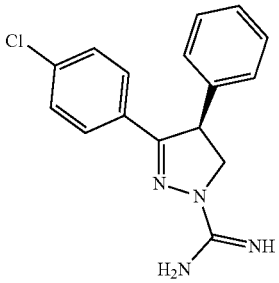 [SMILES: N=C(N)N1C[C@H](c2ccccc2)C(c2ccc(Cl)cc2)=N1]

and the optically active isomer of an acid; and
converting the adduct of the compound

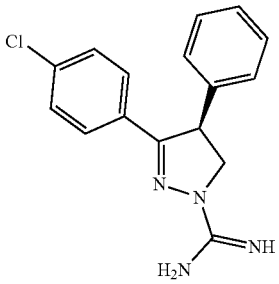

and the optically active isomer of the acid to the compound

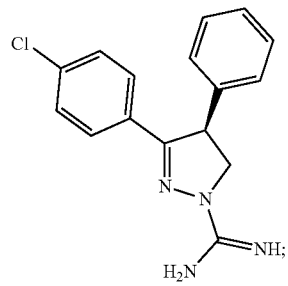 [SMILES: N=C(N)N1C[C@H](c2ccccc2)C(c2ccc(Cl)cc2)=N1]

and
wherein the optically active isomer of the acid is D-aspartic acid.

2. The process according to claim 1, wherein the step of contacting the compound

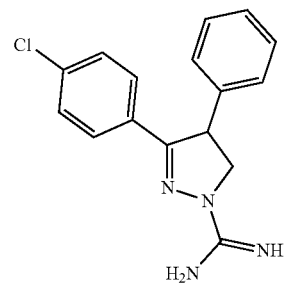 [SMILES: N=C(N)N1CC(c2ccccc2)C(c2ccc(Cl)cc2)=N1]

with the optically active isomer of the acid to form the adduct of the compound

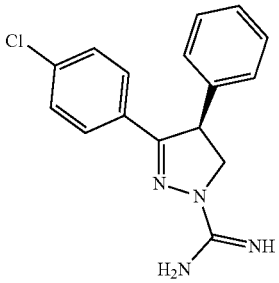 [SMILES: N=C(N)N1C[C@H](c2ccccc2)C(c2ccc(Cl)cc2)=N1]

and the optically active isomer of the acid comprises:
contacting the compound

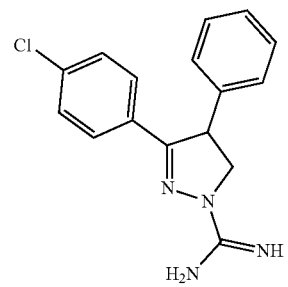

with the optically active isomer of the acid to form the adduct of a compound

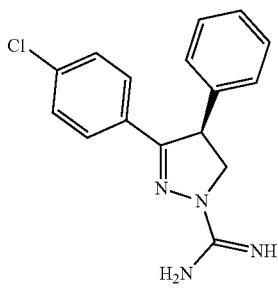 [SMILES: N=C(N)N1C[C@H](c2ccccc2)C(c2ccc(Cl)cc2)=N1]

and the optically active isomer of the acid; and
separating the adduct of the compound

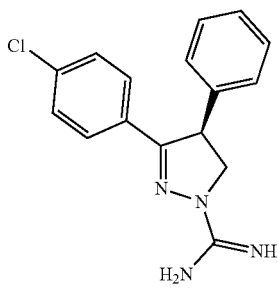 [SMILES: N=C(N)N1C[C@H](c2ccccc2)C(c2ccc(Cl)cc2)=N1]

and the optically active isomer of the acid from its enantiomer.

3. The process according to claim 2, wherein the step of separating the adduct of the compound

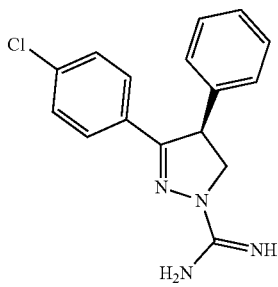 [SMILES: N=C(N)N1C[C@H](c2ccccc2)C(c2ccc(Cl)cc2)=N1]

and the optically active isomer of the acid from its enantiomer is carried out by crystallization of the adduct of the compound

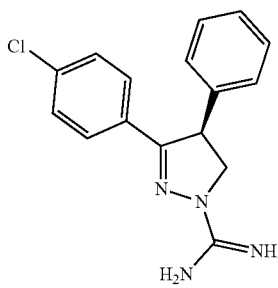 [SMILES: N=C(N)N1C[C@H](c2ccccc2)C(c2ccc(Cl)cc2)=N1]

and the optically active isomer of the acid from a solvent.

4. The process according to claim 3, wherein a diastereomeric excess of the adduct of the compound

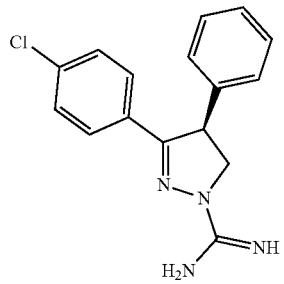 [SMILES: N=C(N)N1C[C@H](c2ccccc2)C(c2ccc(Cl)cc2)=N1]

and the optically active isomer of the acid after crystallization is greater than 95%.

5. The process according to claim 3, wherein the solvent is water, an organic solvent, or a combination thereof.

6. The process according to claim 5, wherein the solvent is water, a C1 to C5 alcohol, or a combination thereof.

7. The process according to claim 1, wherein the step of contacting the compound

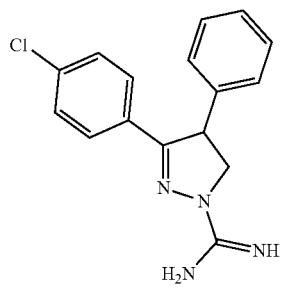 [SMILES: N=C(N)N1CC(c2ccccc2)C(c2ccc(Cl)cc2)=N1]

with the optically active isomer of the acid to form the adduct of the compound

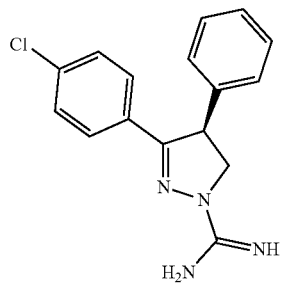 [SMILES: N=C(N)N1C[C@H](c2ccccc2)C(c2ccc(Cl)cc2)=N1]

and the optically active isomer of the acid is preceded by:
reacting compound

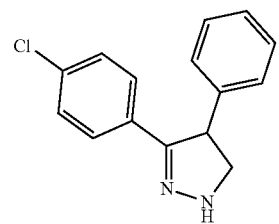 [SMILES: Clc1ccc(C2=NNCC2c2ccccc2)cc1]

with a compound

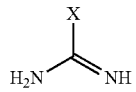

or its salt, wherein X is a first leaving group, to form the compound

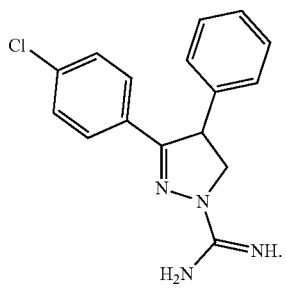 [SMILES: N=C(N)N1CC(c2ccccc2)C(c2ccc(Cl)cc2)=N1]

8. The process according to claim 7, wherein X in the compound

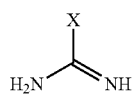

or its salt is S—R, wherein R is a substituted or unsubstituted C1 to C10 alkyl group, a substituted or unsubstituted C3 to C10 cycloalkyl group, a substituted or unsubstituted C6 to C20 aryl group, or a substituted or unsubstituted C3 to C20 heteroaryl group.

9. The process according to claim 8, wherein R is a substituted or unsubstituted C1 to C5 alkyl group.

10. The process according to claim 1, wherein the step of converting the adduct of the compound

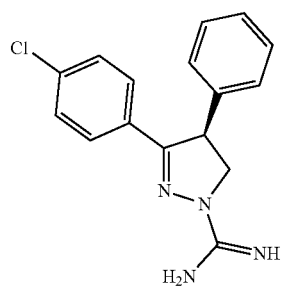 [SMILES: N=C(N)N1C[C@H](c2ccccc2)C(c2ccc(Cl)cc2)=N1]

and the optically active isomer of the acid to the compound

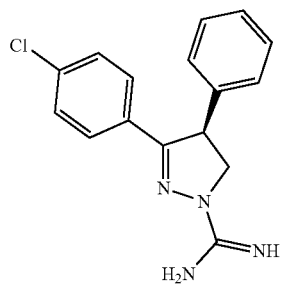 [SMILES: N=C(N)N1C[C@H](c2ccccc2)C(c2ccc(Cl)cc2)=N1]

comprises:
contacting the adduct of the compound

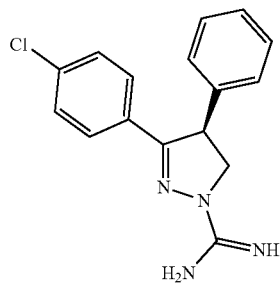 [SMILES: N=C(N)N1C[C@H](c2ccccc2)C(c2ccc(Cl)cc2)=N1]

and the optically active isomer of an acid with a base to form the compound

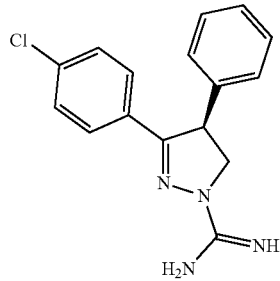 [SMILES: N=C(N)N1C[C@H](c2ccccc2)C(c2ccc(Cl)cc2)=N1]

11. The process according to claim 1, wherein the step of converting the compound

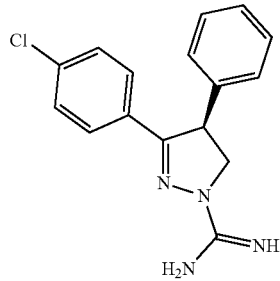 [SMILES: N=C(N)N1C[C@H](c2ccccc2)C(c2ccc(Cl)cc2)=N1]

to (S,1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide comprises:

reacting the compound

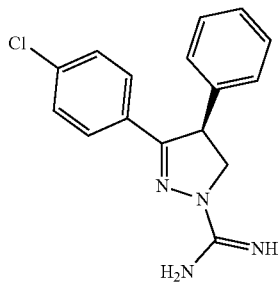 [SMILES: N=C(N)N1C[C@H](c2ccccc2)C(c2ccc(Cl)cc2)=N1]

with a compound

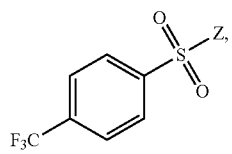

wherein Z is a third leaving group to form a compound

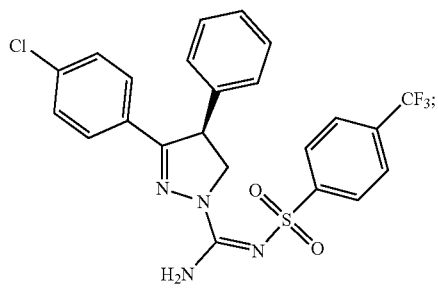 [SMILES: N/C(=N/S(=O)(=O)c1ccc(C(F)(F)F)cc1)N1C[C@H](c2ccccc2)C(c2ccc(Cl)cc2)=N1]

and
reacting the compound

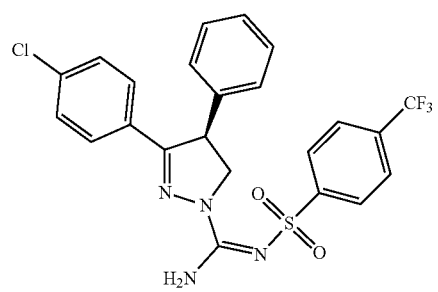 [SMILES: N/C(=N/S(=O)(=O)c1ccc(C(F)(F)F)cc1)N1C[C@H](c2ccccc2)C(c2ccc(Cl)cc2)=N1]

with a compound

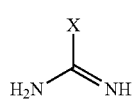

or its salt, wherein X is a first leaving group, to form (S,1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide.

12. The process according to claim 1, wherein the step of converting the compound

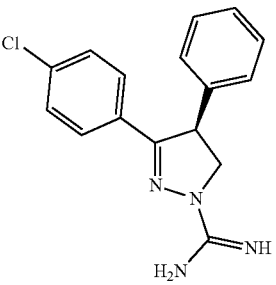 [SMILES: N=C(N)N1C[C@H](c2ccccc2)C(c2ccc(Cl)cc2)=N1]

to (S,1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide comprises:

reacting the compound

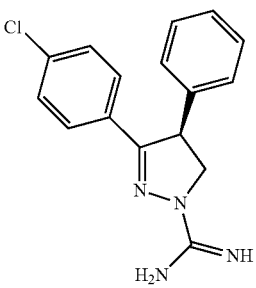 [SMILES: N=C(N)N1C[C@H](c2ccccc2)C(c2ccc(Cl)cc2)=N1]

with compound

or its salt, wherein Y is a second leaving group, to form compound

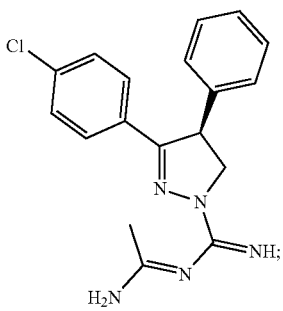 [SMILES: C/C(N)=N\C(=N)N1C[C@H](c2ccccc2)C(c2ccc(Cl)cc2)=N1]

and reacting the compound

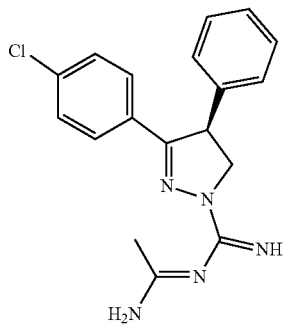 [SMILES: C/C(N)=N\C(=N)N1C[C@H](c2ccccc2)C(c2ccc(Cl)cc2)=N1]

with a compound

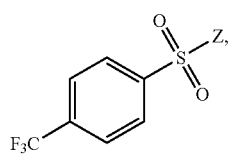

wherein Z is a third leaving group, to form (S,1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide.

13. The process according to claim 12, wherein Y in the compound

or its salt is X—R, wherein X is O or S, and R is a substituted or unsubstituted C1 to C10 alkyl group, a substituted or unsubstituted C3 to C10 cycloalkyl group, a substituted or unsubstituted C2 to C10 alkanoyl group, a substituted or unsubstituted C4 to C10 cycloalkanoyl group, a substituted or unsubstituted C6 to C20 aryl group, or a substituted or unsubstituted C3 to C20 heteroaryl group.

14. The process according to claim 13, wherein R is a substituted or unsubstituted C1 to C5 alkyl group.

15. The process according to claim 11, wherein Z in the compound

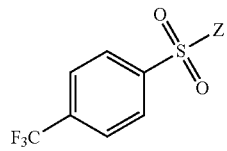

is a halide.

16. The process according to claim 2, wherein (S,1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide is purified by a recrystallization from an organic solvent, and wherein a purity of (S,1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide after the recrystallization is greater than 98.5%.

17. A process for the preparation of (S,1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide, the process comprising:

Step (a): reacting a compound

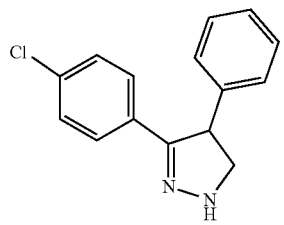 [SMILES: Clc1ccc(C2=NNCC2c2ccccc2)cc1]

with a compound

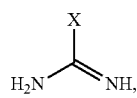

wherein X is a first leaving group, to form a compound

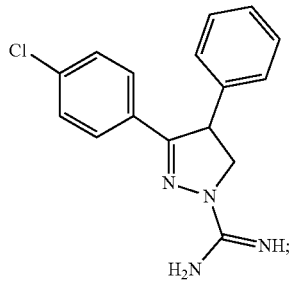 [SMILES: N=C(N)N1CC(c2ccccc2)C(c2ccc(Cl)cc2)=N1]

Step (b): contacting the compound

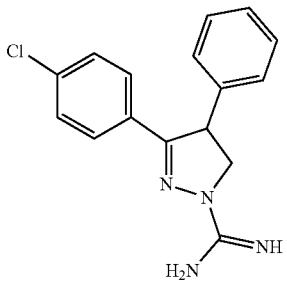 [SMILES: N=C(N)N1CC(c2ccccc2)C(c2ccc(Cl)cc2)=N1]

with an optically active isomer of an acid to form an adduct of a compound

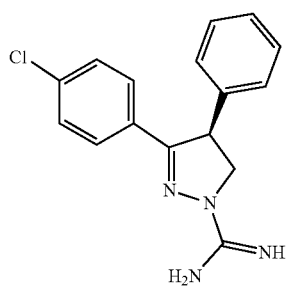 [SMILES: N=C(N)N1C[C@H](c2ccccc2)C(c2ccc(Cl)cc2)=N1]

and an acid salt;

Step (c): separating the adduct of the compound

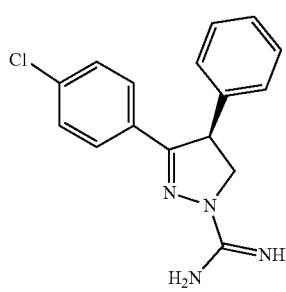 [SMILES: N=C(N)N1C[C@H](c2ccccc2)C(c2ccc(Cl)cc2)=N1]

and the optically active isomer of the acid from its enantiomer;

Step (d): contacting the adduct of the compound

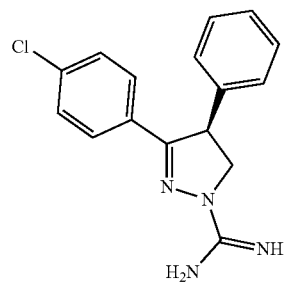 [SMILES: N=C(N)N1C[C@H](c2ccccc2)C(c2ccc(Cl)cc2)=N1]

and the optically active isomer of the acid with a base to form compound

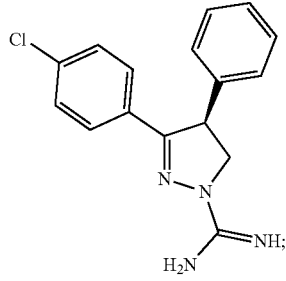 [SMILES: N=C(N)N1C[C@H](c2ccccc2)C(c2ccc(Cl)cc2)=N1]

Step (e): converting the compound

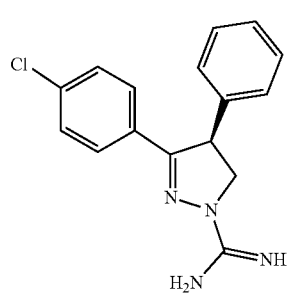 [SMILES: N=C(N)N1C[C@H](c2ccccc2)C(c2ccc(Cl)cc2)=N1]

to (S,1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide;
wherein Step (e) comprises:
Step (f): reacting the compound

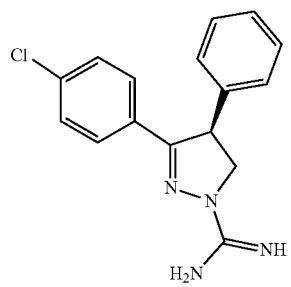 [SMILES: N=C(N)N1C[C@H](c2ccccc2)C(c2ccc(Cl)cc2)=N1]

with compound

wherein Y is a second leaving group, to form compound

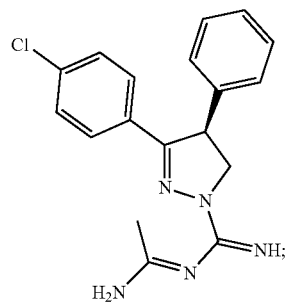 [SMILES: C/C(N)=N\C(=N)N1C[C@H](c2ccccc2)C(c2ccc(Cl)cc2)=N1]

Step (g): reacting the compound

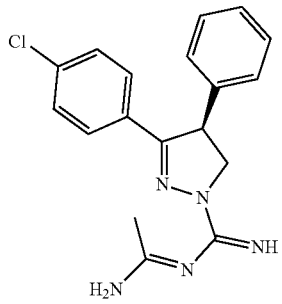 [SMILES: C/C(N)=N\C(=N)N1C[C@H](c2ccccc2)C(c2ccc(Cl)cc2)=N1]

with a compound

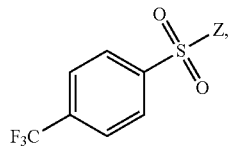

wherein Z is a third leaving group, to form (S,1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide;

wherein Step (e) comprises:

Step (f): reacting the compound

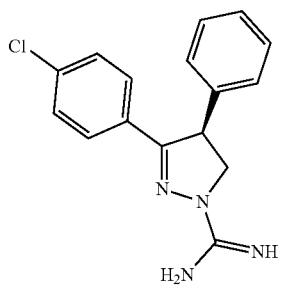 [SMILES: N=C(N)N1C[C@H](c2ccccc2)C(c2ccc(Cl)cc2)=N1]

with a compound

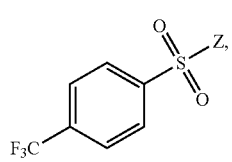

wherein Z is a third leaving group to form a compound

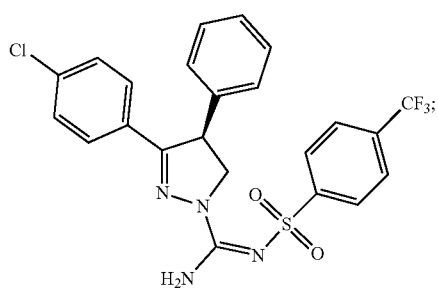 [SMILES: N/C(=N/S(=O)(=O)c1ccc(C(F)(F)F)cc1)N1C[C@H](c2ccccc2)C(c2ccc(Cl)cc2)=N1]

and

Step (g): reacting the compound

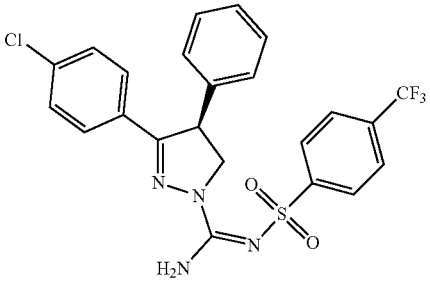 [SMILES: N/C(=N/S(=O)(=O)c1ccc(C(F)(F)F)cc1)N1C[C@H](c2ccccc2)C(c2ccc(Cl)cc2)=N1]

with a compound

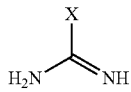

or its salt, wherein X is a first leaving group, to form (S,1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide, and wherein X is S—$CH_3$, Y is O—$C_2H_5$, and Z is Cl.

18. A process for the preparation of (S,1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide, comprising the steps of:

reacting 4-(trifluoromethyl)benzenesulfonamide with ethyl chloroformate to form ethyl (4-(trifluoromethyl)phenyl) sulfonylcarbamate;

reacting ethyl (4-(trifluoromethyl)phenyl) sulfonylcarbamate with compound

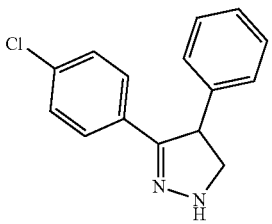 [SMILES: Clc1ccc(C2=NNCC2c2ccccc2)cc1]

to form compound

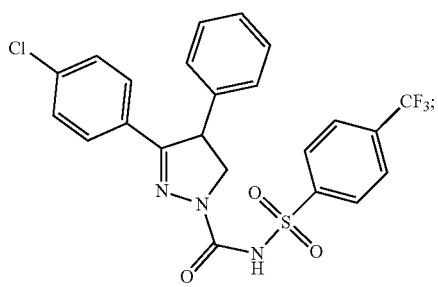 [SMILES: O=C(NS(=O)(=O)c1ccc(C(F)(F)F)cc1)N1CC(c2ccccc2)C(c2ccc(Cl)cc2)=N1]

reacting the compound

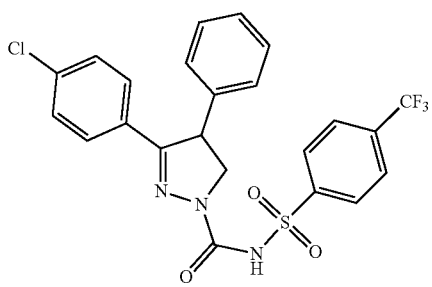 [SMILES: O=C(NS(=O)(=O)c1ccc(C(F)(F)F)cc1)N1CC(c2ccccc2)C(c2ccc(Cl)cc2)=N1]

with phosphorus oxychloride to form compound

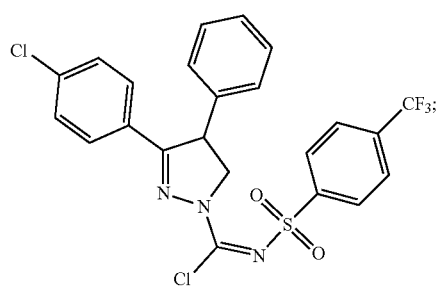 [SMILES: O=S(=O)(/N=C(/Cl)N1CC(c2ccccc2)C(c2ccc(Cl)cc2)=N1)c1ccc(C(F)(F)F)cc1]

and
converting the compound

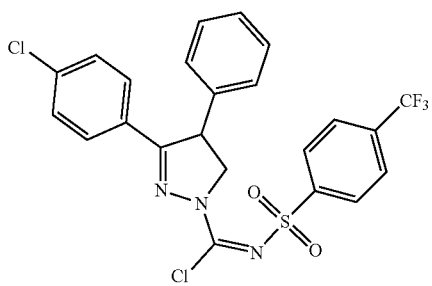 [SMILES: O=S(=O)(/N=C(/Cl)N1CC(c2ccccc2)C(c2ccc(Cl)cc2)=N1)c1ccc(C(F)(F)F)cc1]

to (1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide, wherein the step of converting the compound

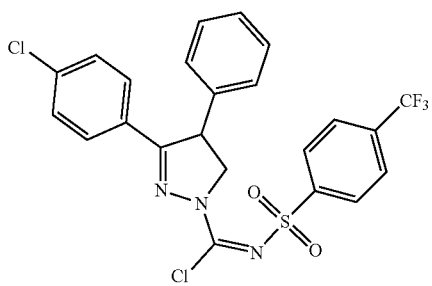 [SMILES: O=S(=O)(/N=C(/Cl)N1CC(c2ccccc2)C(c2ccc(Cl)cc2)=N1)c1ccc(C(F)(F)F)cc1]

to (1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide comprises:

reacting the compound

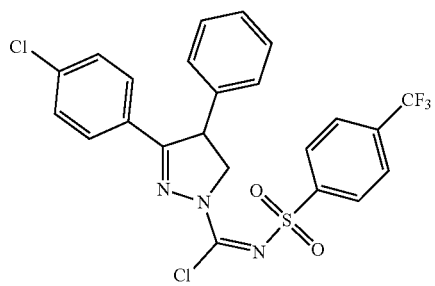 [SMILES: O=S(=O)(/N=C(/Cl)N1CC(c2ccccc2)C(c2ccc(Cl)cc2)=N1)c1ccc(C(F)(F)F)cc1]

with an acetimidamide agent in a solvent system comprising iso-propanol and dichloromethane to form (1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide.

19. A process for the preparation of (1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide, comprising the steps of:

providing a compound

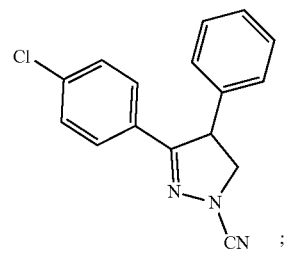 [SMILES: N#CN1CC(c2ccccc2)C(c2ccc(Cl)cc2)=N1]

and
converting the compound

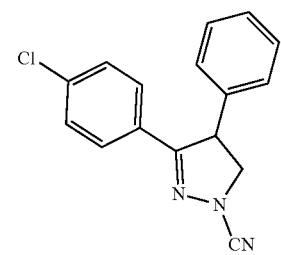 [SMILES: N#CN1CC(c2ccccc2)C(c2ccc(Cl)cc2)=N1]

to (1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide, wherein the step of converting the compound

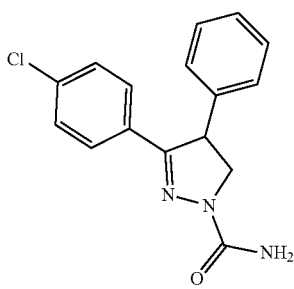 [SMILES: NC(=O)N1CC(c2ccccc2)C(c2ccc(Cl)cc2)=N1]

to the compound

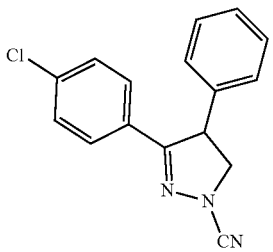 [SMILES: N#CN1CC(c2ccccc2)C(c2ccc(Cl)cc2)=N1]

is carried out by contacting the compound

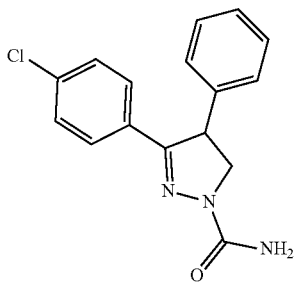 [SMILES: NC(=O)N1CC(c2ccccc2)C(c2ccc(Cl)cc2)=N1]

with a dehydrating agent.

20. The process according to claim 19, wherein the step of providing a compound

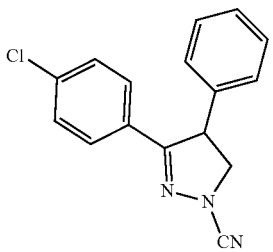 [SMILES: N#CN1CC(c2ccccc2)C(c2ccc(Cl)cc2)=N1]

comprises:
converting a compound

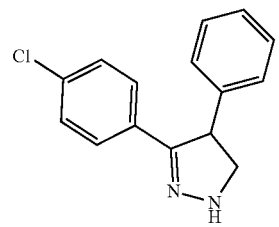 [SMILES: Clc1ccc(C2=NNCC2c2ccccc2)cc1]

to a compound

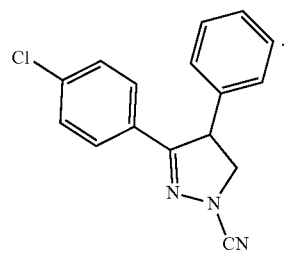 [SMILES: N#CN1CC(c2ccccc2)C(c2ccc(Cl)cc2)=N1]

21. The process according to claim 19, wherein the step of converting the compound

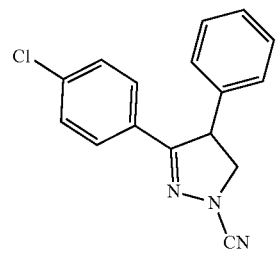 [SMILES: N#CN1CC(c2ccccc2)C(c2ccc(Cl)cc2)=N1]

to (1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide comprises:
reacting the compound

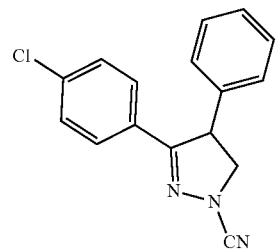 [SMILES: N#CN1CC(c2ccccc2)C(c2ccc(Cl)cc2)=N1]

with an acetimidamide agent to form a compound

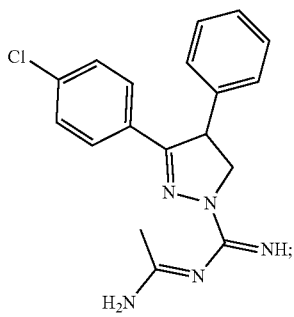 [SMILES: C/C(N)=N\C(=N)N1CC(c2ccccc2)C(c2ccc(Cl)cc2)=N1]

and
reacting the compound

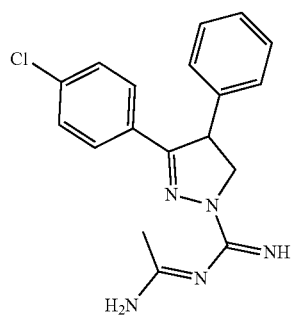 [SMILES: C/C(N)=N\C(=N)N1CC(c2ccccc2)C(c2ccc(Cl)cc2)=N1]

with a compound

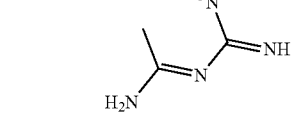

wherein Z is a third leaving group, to form (1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide.

22. The process according to claim 19, wherein the step of converting the compound

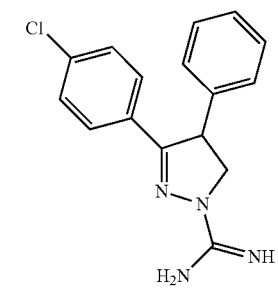 [SMILES: N=C(N)N1CC(c2ccccc2)C(c2ccc(Cl)cc2)=N1]

to (1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide comprises:

reacting the compound

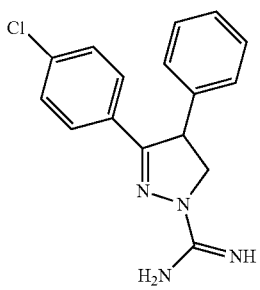 [SMILES: N=C(N)N1CC(c2ccccc2)C(c2ccc(Cl)cc2)=N1]

with a compound

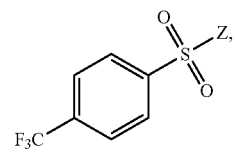

wherein Z is a leaving group to form a compound

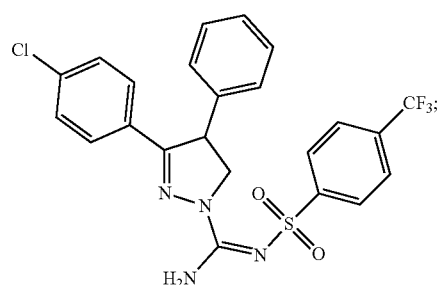

and
reacting the compound

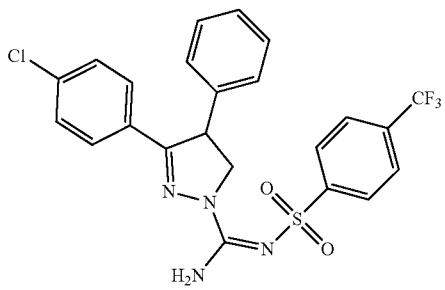 [SMILES: N/C(=N/S(=O)(=O)c1ccc(C(F)(F)F)cc1)N1CC(c2ccccc2)C(c2ccc(Cl)cc2)=N1]

with a compound

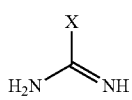

or its salt, wherein X is a first leaving group, to form (1E,NE)-N-(1-aminoethylidene)-3-(4-chlorophenyl)-4-phenyl-N'-((4-(trifluoromethyl)phenyl) sulfonyl)-4,5-dihydro-1H-pyrazole-1-carboximidamide.

23. A compound represented by one the following formulae or its enantiomer:
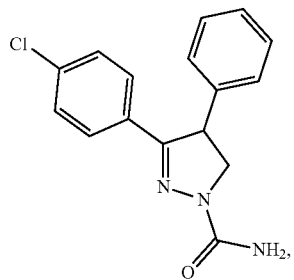
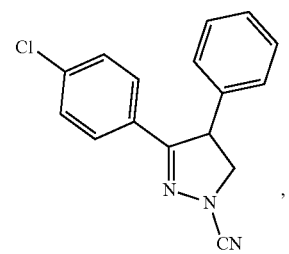,
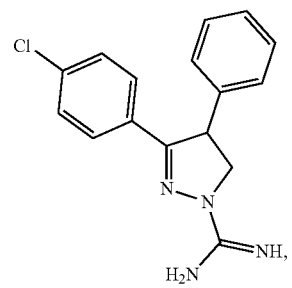,
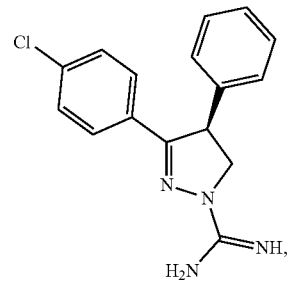,
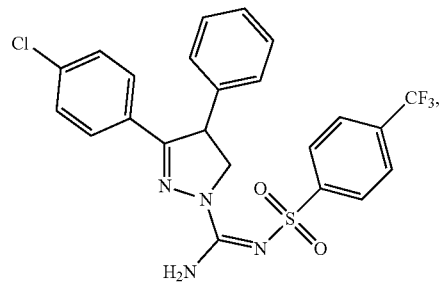
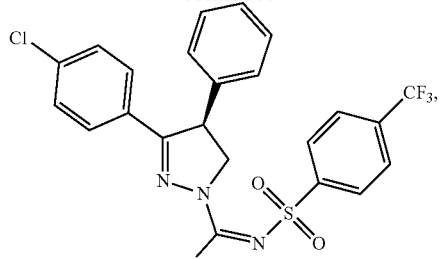,
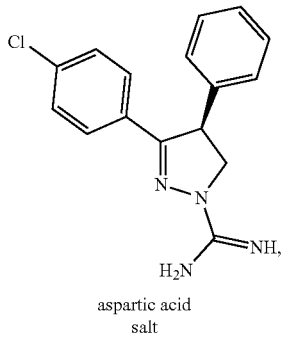,
aspartic acid salt
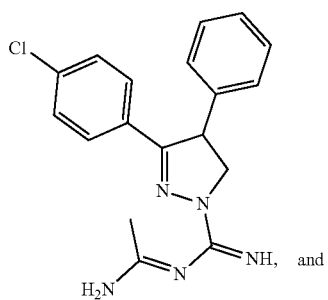 and
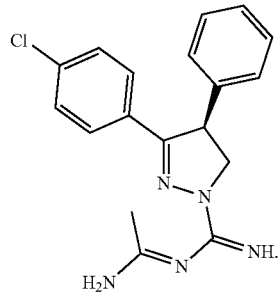.
24. The process according to claim 12, wherein Z in the compound
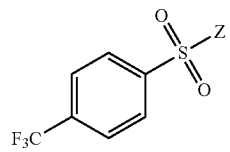
is a halide.
* * * * *